(12) United States Patent
Jiang et al.

(10) Patent No.: US 8,710,098 B2
(45) Date of Patent: Apr. 29, 2014

(54) GROUP OF AMINO SUBSTITUTED BENZOYL DERIVATIVES AND THEIR PREPARATION AND THEIR USE

(75) Inventors: Jian-Dong Jiang, Beijing (CN); Liyan Yu, Beijing (CN); Shan Cen, Beijing (CN); Zhuorong Li, Beijing (CN); Yanping Li, Beijing (CN); Jian Xu, Beijing (CN)

(73) Assignee: Institute of Medicinal Biotechnology Chinese Academy of Medical Science, Beijing (CN)

(*) Notice: Subject to any disclaimer, the term of this patent is extended or adjusted under 35 U.S.C. 154(b) by 64 days.

(21) Appl. No.: 12/998,210

(22) PCT Filed: Sep. 28, 2009

(86) PCT No.: PCT/CN2009/001094
§ 371 (c)(1),
(2), (4) Date: Mar. 25, 2011

(87) PCT Pub. No.: WO2010/037271
PCT Pub. Date: Apr. 8, 2010

(65) Prior Publication Data
US 2011/0178108 A1    Jul. 21, 2011

(30) Foreign Application Priority Data
Sep. 28, 2008   (CN) .......................... 2008 1 0168824

(51) Int. Cl.
*A01N 47/10*   (2006.01)
*A61K 31/34*   (2006.01)
*C07D 239/02*  (2006.01)
*C07C 261/00*  (2006.01)
*C07C 269/00*  (2006.01)
*C07C 271/00*  (2006.01)
*C07C 229/00*  (2006.01)
*C07C 239/00*  (2006.01)

(52) U.S. Cl.
USPC ............. 514/486; 514/535; 544/319; 560/29; 560/46; 564/139; 564/155

(58) Field of Classification Search
None
See application file for complete search history.

(56) References Cited

U.S. PATENT DOCUMENTS 6,521,658 B1 *   2/2003   Li et al. .......................... 514/415
2008/0234273 A1 *   9/2008   McKerrecher et al. ..... 514/236.8

FOREIGN PATENT DOCUMENTS

WO         WO0102350 A2        1/2001

OTHER PUBLICATIONS

Hu et al. (Bioorg Med Chem Lett. Dec. 15, 2007;17(24):6847-52. Epub Oct. 17, 2007).*
Mutational Alteration of Human Immunodeficiency Virus Type 1 Vif Allows for Functional Interaction with Nonhuman Primate APOBEC3G†; Journal of Virology, Jun. 2006, p. 5984-599.
Novel Sulfonate Analogues of Combretastatin A-4: Potent Antimitotic Agents; Biorganic & Medicinal Chemistry Letters 11 (2001) pp. 871-874.
Small-Molecule Inhibition of HIV-1 Vif; Nature Biotechnology 2008, Robin Nathans, published online Sep. 21, 2008.
Cytidine deamination and resistance to retroviral infections: Towards a structural understanding of the APOBEC proteins; Elsevier/Virology, Hendrik Huthoff, Jan. 27, 2005.
International Search Report issued Dec. 21, 2009 in counterpart foreign application under the WIPO, Application No. PCT/CN2009/001094.

* cited by examiner

*Primary Examiner* — James D Anderson
*Assistant Examiner* — William Lee
(74) *Attorney, Agent, or Firm* — Andrews Kurth LLP; Sean S. Wooden

(57) ABSTRACT

A group of amino substituted benzoyl derivatives, their preparation and their use. The screening and research on an antiviral drug with hA3G/Vif as a target point proves that the 3-amino benzoyl derivatives not only have the combined activity for the hA3G/Vif, but also have a function of inhibiting replication of viruses. The present invention provides the possible breakthrough progress for the problem of HIV drug resistance, thereby providing a novel clinical antiviral drug which has higher efficiency.

3 Claims, No Drawings

GROUP OF AMINO SUBSTITUTED BENZOYL DERIVATIVES AND THEIR PREPARATION AND THEIR USE

FIELD

This invention involves a group of amino substituted benzoyl derivatives, the preparation methods of said derivatives and their applications in anti-virus, as well as the pharmaceutical compositions of said derivatives.

BACKGROUND

Presently, all the targets of clinically applied anti-virus drugs are viral proteins. The functioning mechanism of these drugs is to inhibit the replication of the virus or to block the invasion of the virus. The viruses are "moving targets", they will perpetually vary themselves to elude the attack of the drugs. It is a world scale conundrum that the variations of viruses induced by the drugs targeting the viral proteins and resulting in the resistance to drugs. In the same way, the targets of the anti-AIDS virus drugs using currently in common clinic are the HIV viral proteins too. They will cause severe problem of the resistance to drugs and subsequently failure of the remedy. Multidrug therapy (MDT, cocktail therapy) can greatly decrease virus stock and retard the occurrence of resistance to drugs, however, still the occurrence of resistance to drugs will finally be inevasible. The newly marketed variety of drugs has possessed some advantages against the virus strains with resistance to drugs, nevertheless, as prolonged application in clinic, the resistance to drugs is still unavoidable. Therefore, it is a presently primary topic to tackle the problem of resistance to drugs.

Along with ever-deepening development of the researches on virology and cell biology, vast amount of research results demonstrated that the host cells universally form their own defending system against different pathologic viruses during the endless course of organic evolution, and the viruses form also specific antagonistic mechanism for their own to evade the inhibition effect from the host cells. Presently, the relationships of mutual dependence and antagonism between viruses and host cells, especially those relating to HIV-1 cytokines, have become the leading edge and most rapidly developing area in the researches of fundamentals and applications of medical chemistry.

Vif (virion infectivity factor) is the viral protein coded by HIV-1 genome, it plays a key role in HIV-1 replication and infection. Recent researches have demonstrated that hA3G related closely to the biological function of Vif. hA3G is a kind of RNA/DNA editing enzyme expressed in human lymphocytes and is a member of the APOBEC protein superfamily. APOBEC3G belongs to APOBEC family. The most recent results of research showed that APOBEC3G protein may induce G to A hypermutability of HIV-1 virus genome and inhibit virus replication with high efficiency. It is an anti-virus cellular factor naturally produced in host cells.

Anti-virusantiviral screening researches using hA3G/Vif interaction as target demonstrated that 3-amino benzoyl derivatives have the activity to inhibit the interaction process of hA3G/Vif and the replication of the viruses. These compounds put forward in this invention and their functions have not been found in the literature in China and abroad up to now. The development of new anti-virus compounds aiming at a newnovel drug target hA3G may make a breakthrough at solving the problem about HIV with resistance to drugs, thereby can provide more effective new anti-virusantiviral drugs for clinic.

A main object of this invention is to screen out a new kind of anti-virus compounds and their pharmaceutically salts aiming at hA3G/Vif interaction as the target via the structure-activity research on a group of amino benzoyl derivatives. Not only this kind of compounds inhibits the hA3G/Vif conjugation interaction binding, but it possesses significant anti-virus activity.

SUMMARY

This invention provides a group of amino-benzoyl derivatives.

This invention provides the methods for preparing said derivatives.

This invention provides the pharmaceutical compositions containing said amino-benzoyl derivatives as the active components.

This invention further provides the anti-virus application of said amino-benzoyl derivatives and their pharmaceutically salts, especially in the treatment of HIV infection, including the applications combined with other anti-virus chemotherapy drugs.

This invention firstly provides the amino-benzoyl derivatives with following general formula (I) and their pharmaceutically salts.

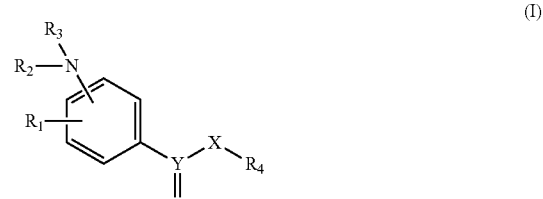

Wherein $R_1$ is H, or one or more of the following groups on the benzene ring: nitro-, halido-, cyano-, ester-, amido-, hydroxo-, mercapto-, substituted or non-substituted low alkyl-, low alkoxy- or aryloxy-, low alkylthio- or arylthio-, amino- or substituted amino groups and so on;

$R_2$, $R_3$ may be identical or different, they may individually be H, low alkyl, carbonyl or sulfonyl groups;

X is O, S, NH, $NR_5$, $CH_2$ or $CHR_6$;

Y is C, S or SO;

$R_4$ and $R_5$ individually is H, low alkyl, hydroxyl, aryl or substituted aryl groups;

The amino substituted derivatives of this invention according to the general formula (I) include their salts with acids. The examples of the salts are those formed by the said compounds with inorganic acids, such as chloride, bromide and, sulfate, etc, or with organic acids, such as acetate, lactate, succinate, fumarate, maleate, citrate, benzoate, methanesulfonate and p-benzoate and so on.

The amino substituted-benzoyl derivatives defined in this invention are screened out from large amount of candidate compounds, the non-limited examples of the structures is as follows:

1
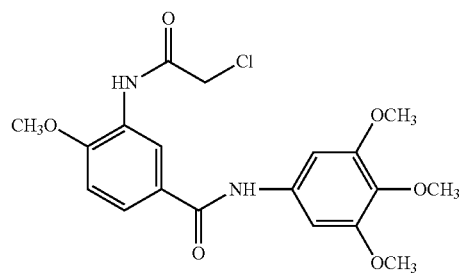
262
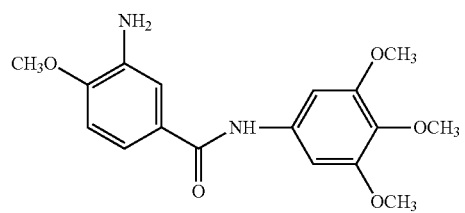
3
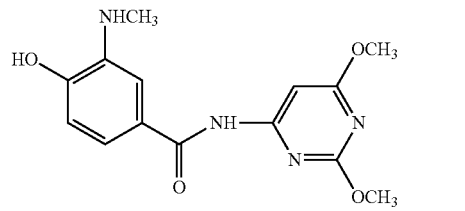
4
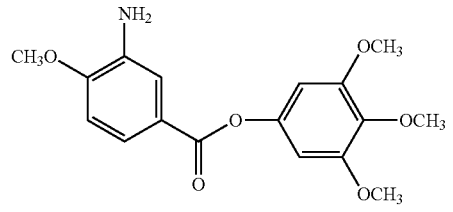
5
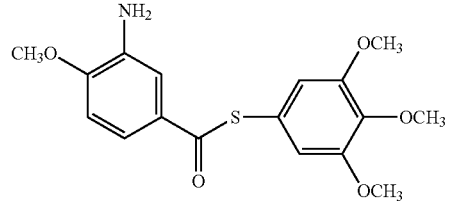
6
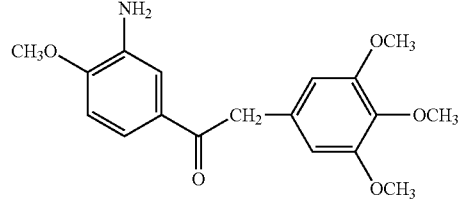
261
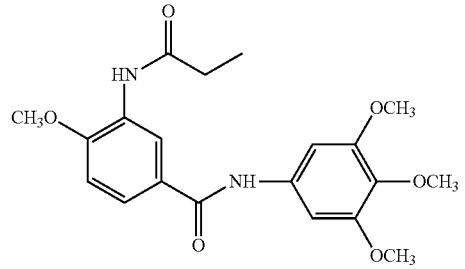
351
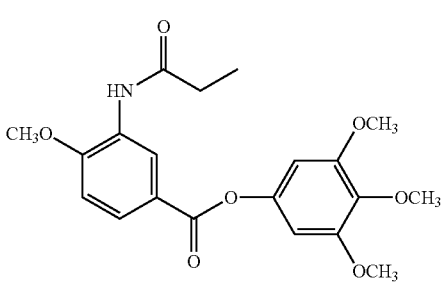
9
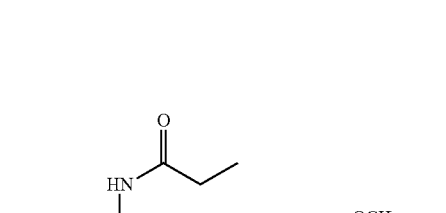
10
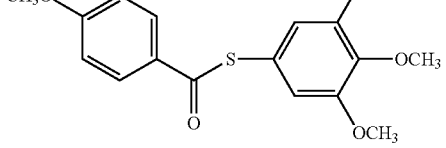
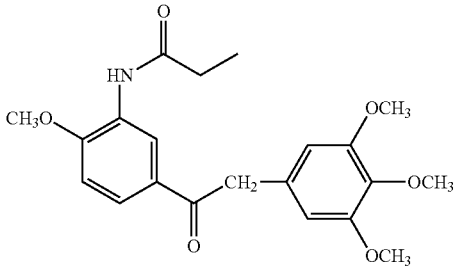
11
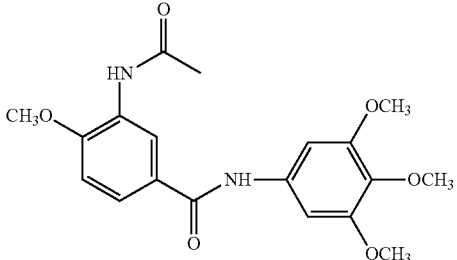
12
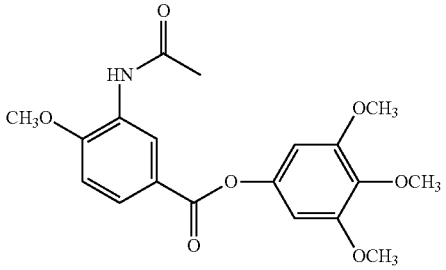

13
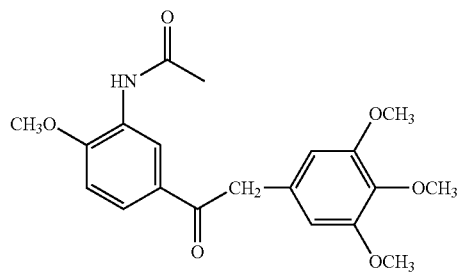
14
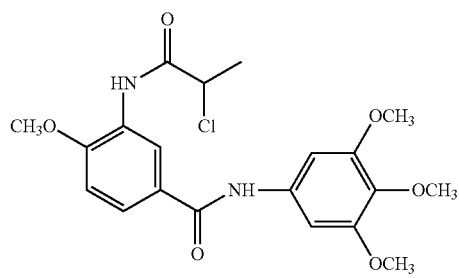
15
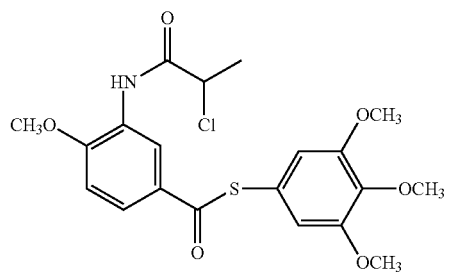
16
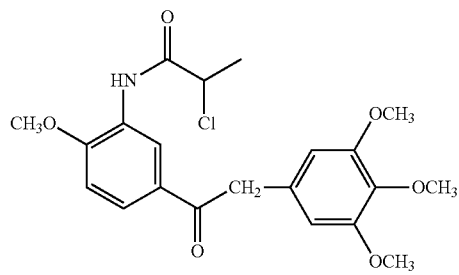
17
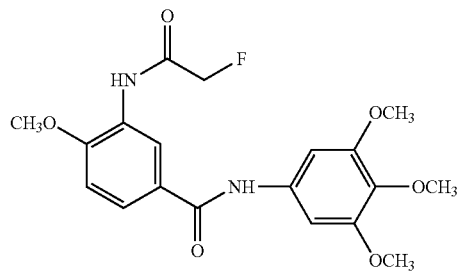
18
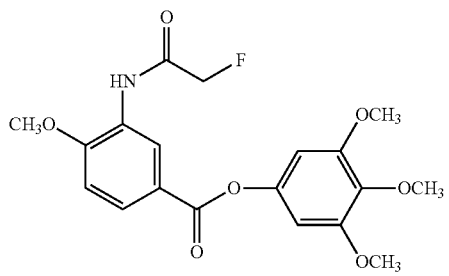
19
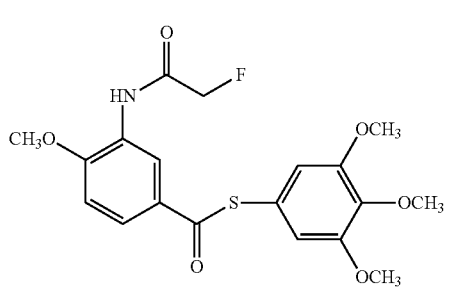
20
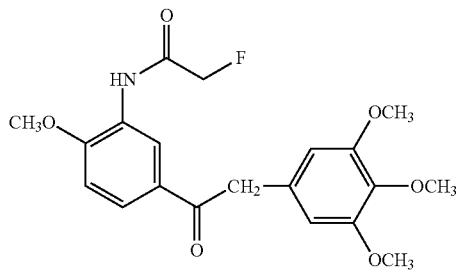
21
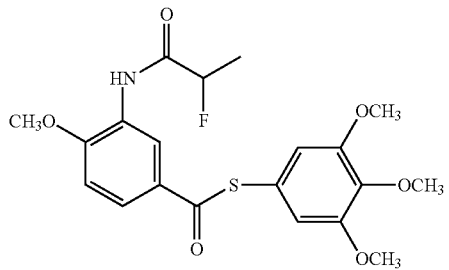
22
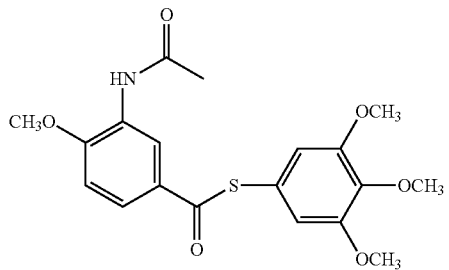

23
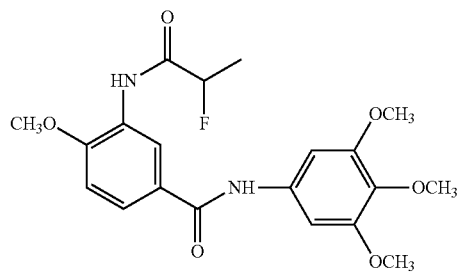
24
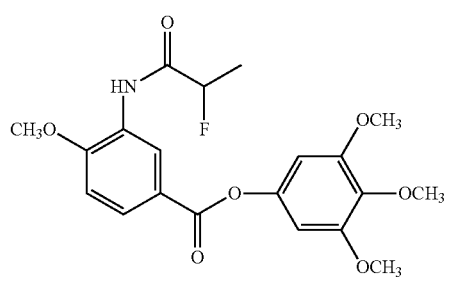
25
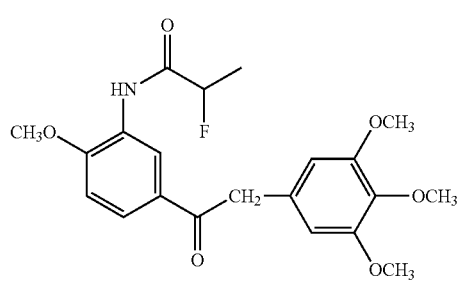
26
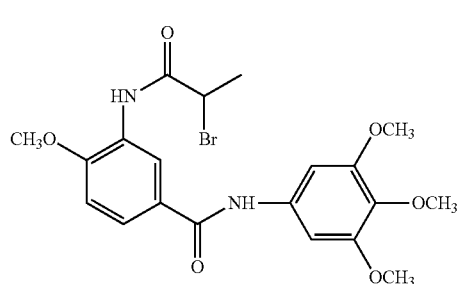
27
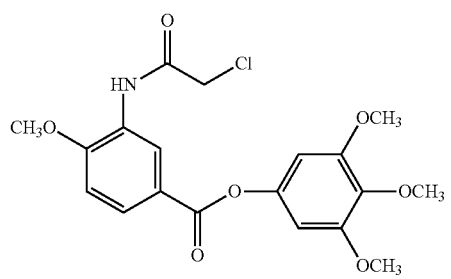
28
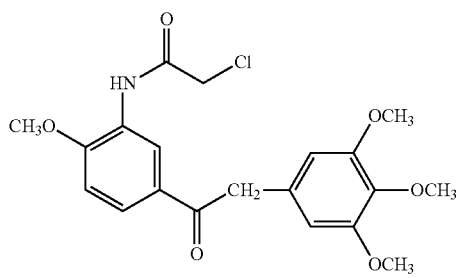
29
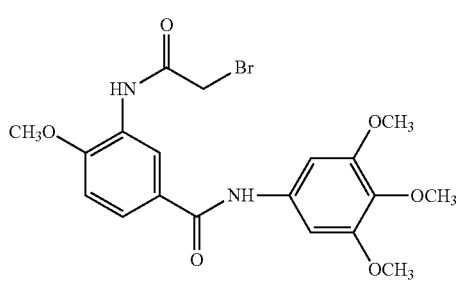
30
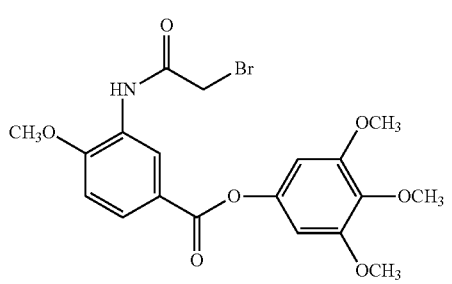
31
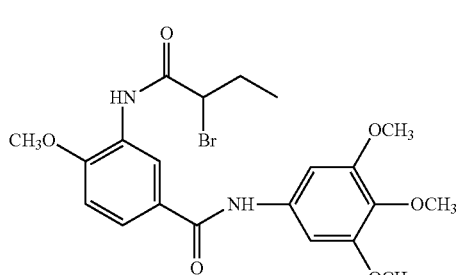
32
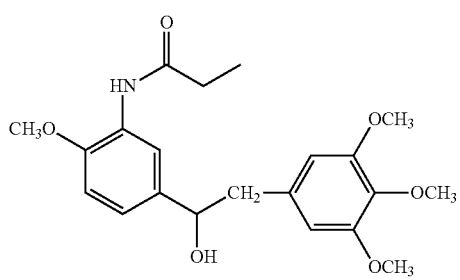

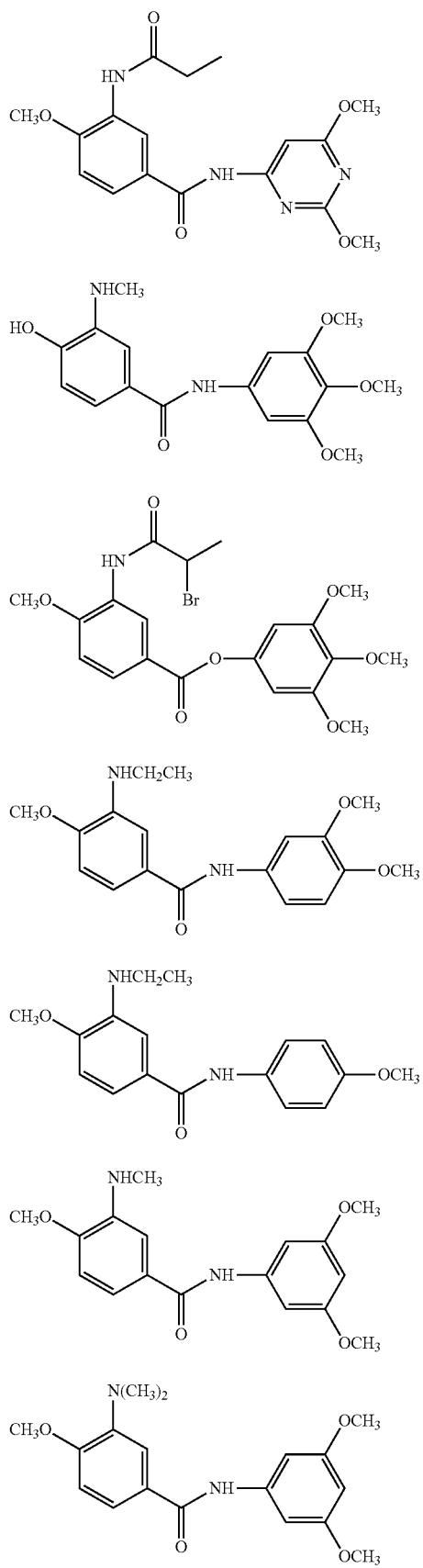
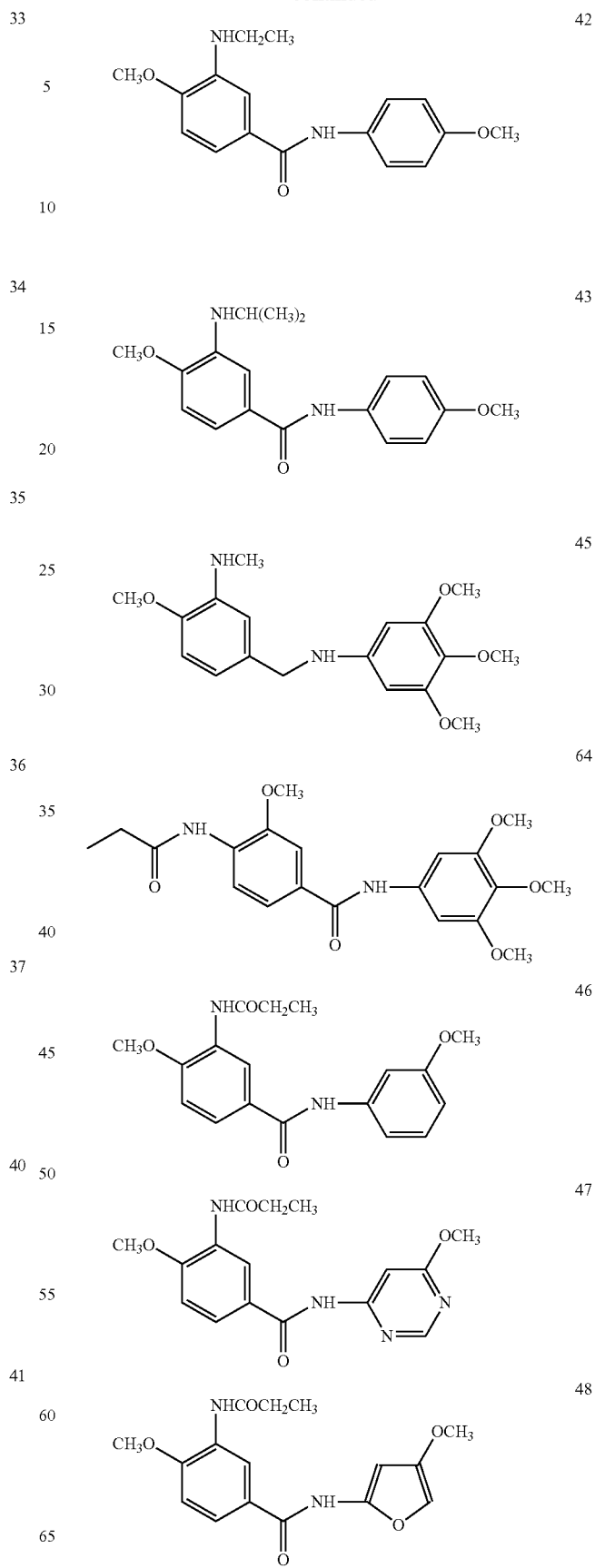

49
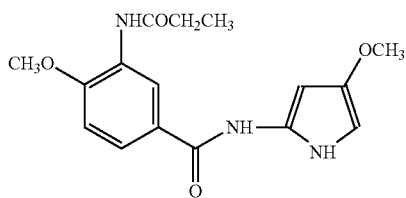
50
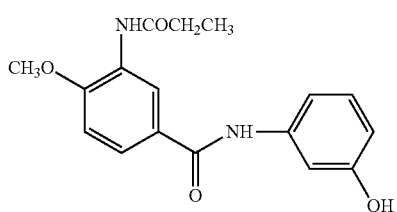
51
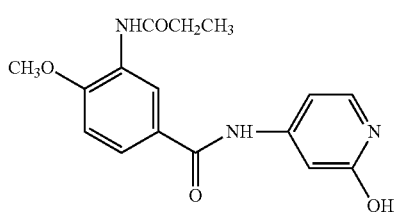
52
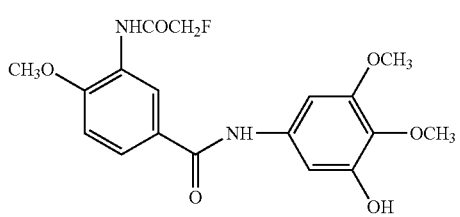
53
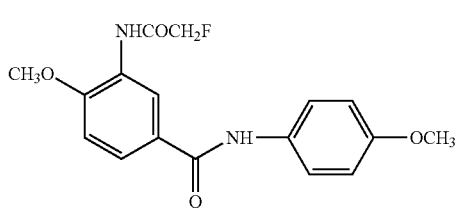
54
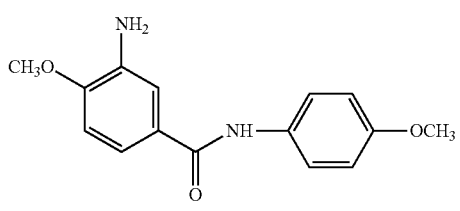
55
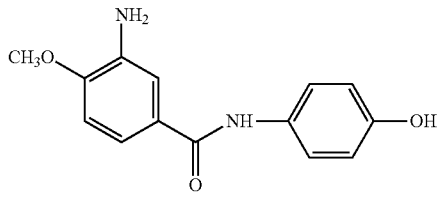
56
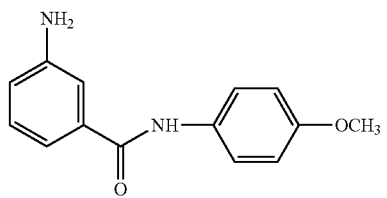
57
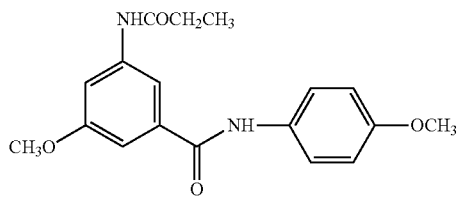
58
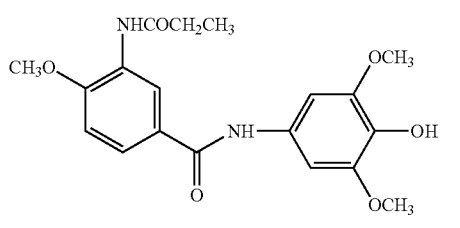
59
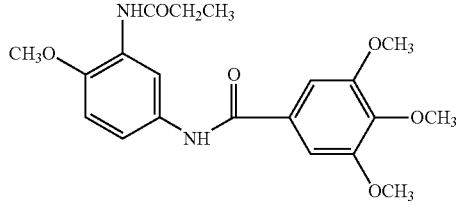
60
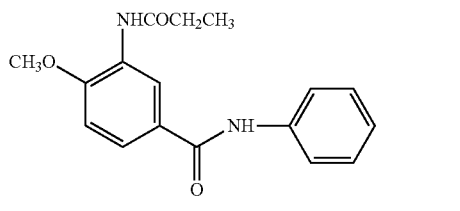
61
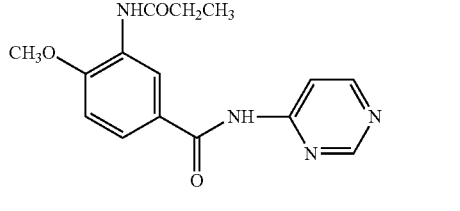
62
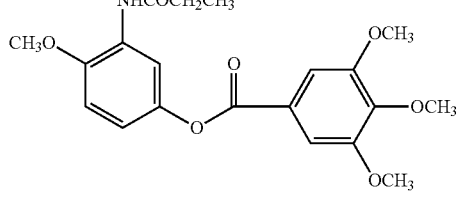

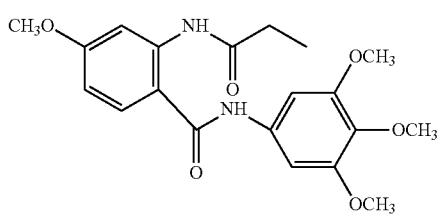
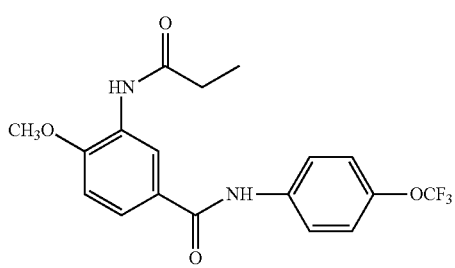
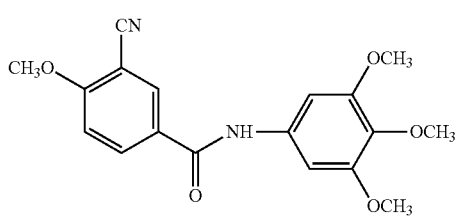
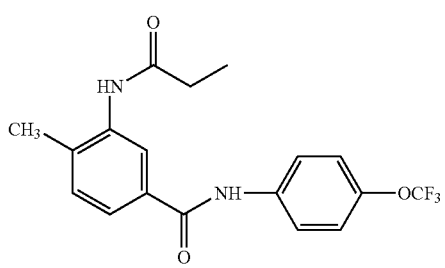
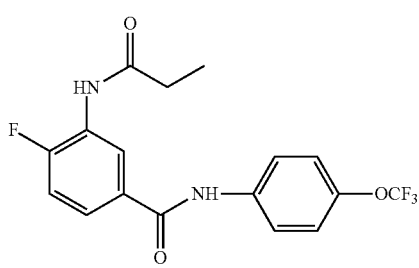
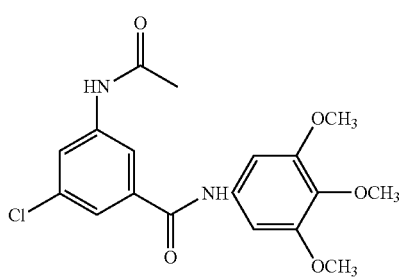
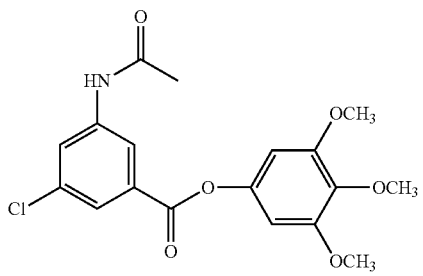
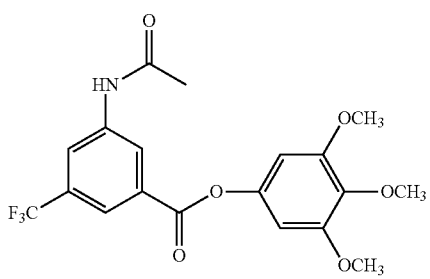
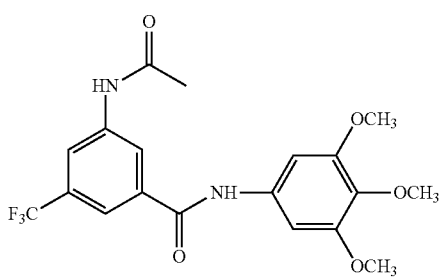
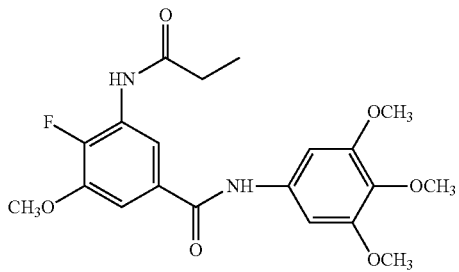
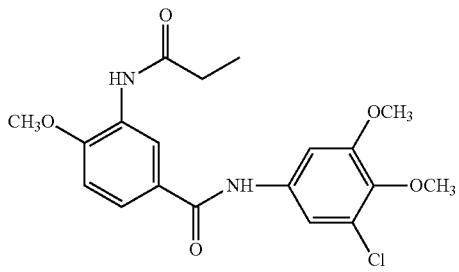

77
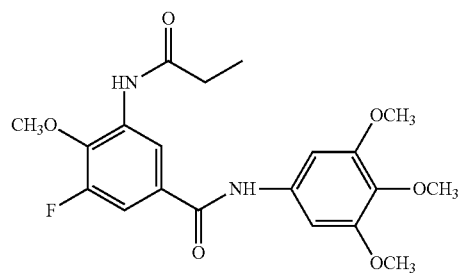
78
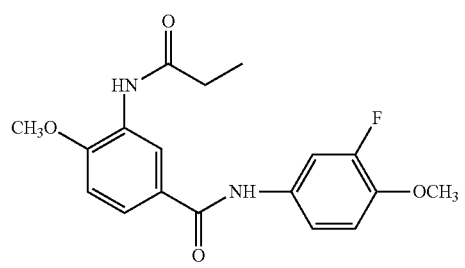
79
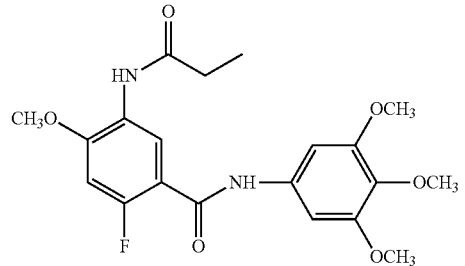
80
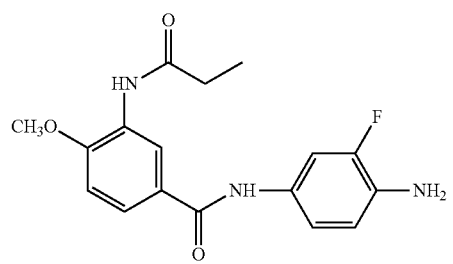
81
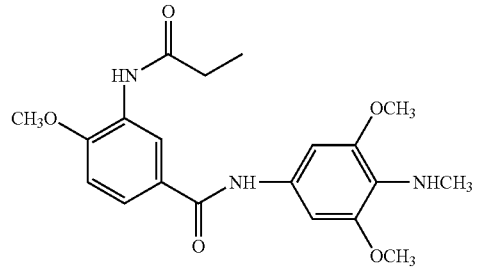
82
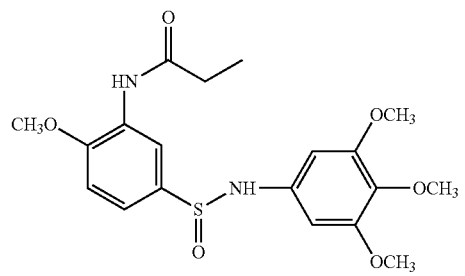
83
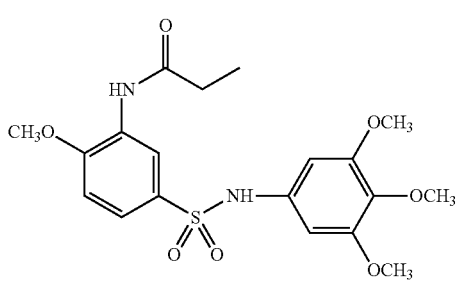
84
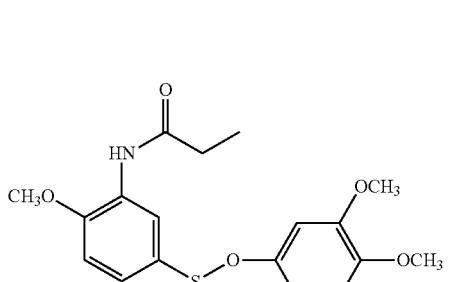
85
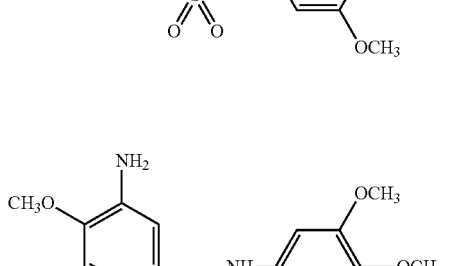
86
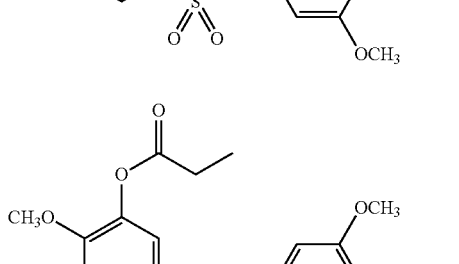
87
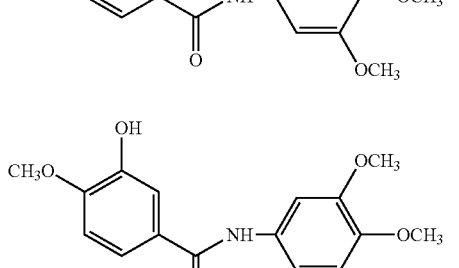
88
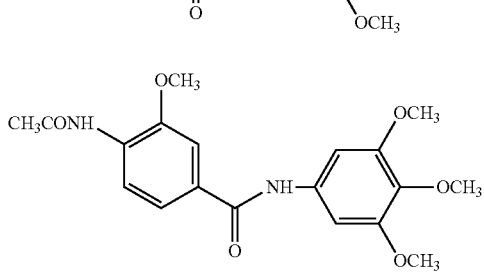

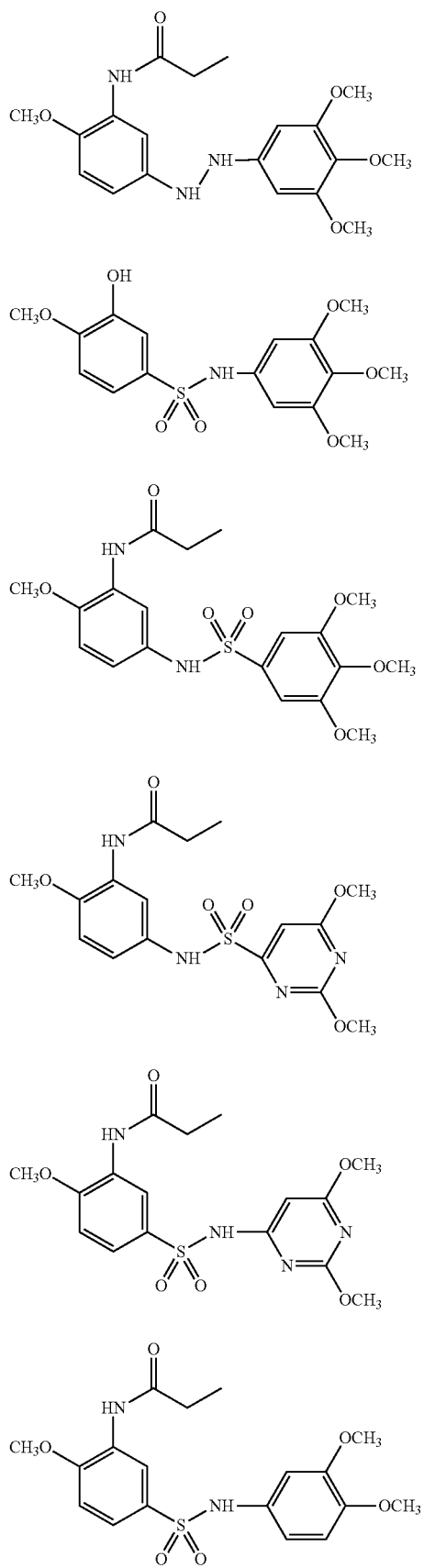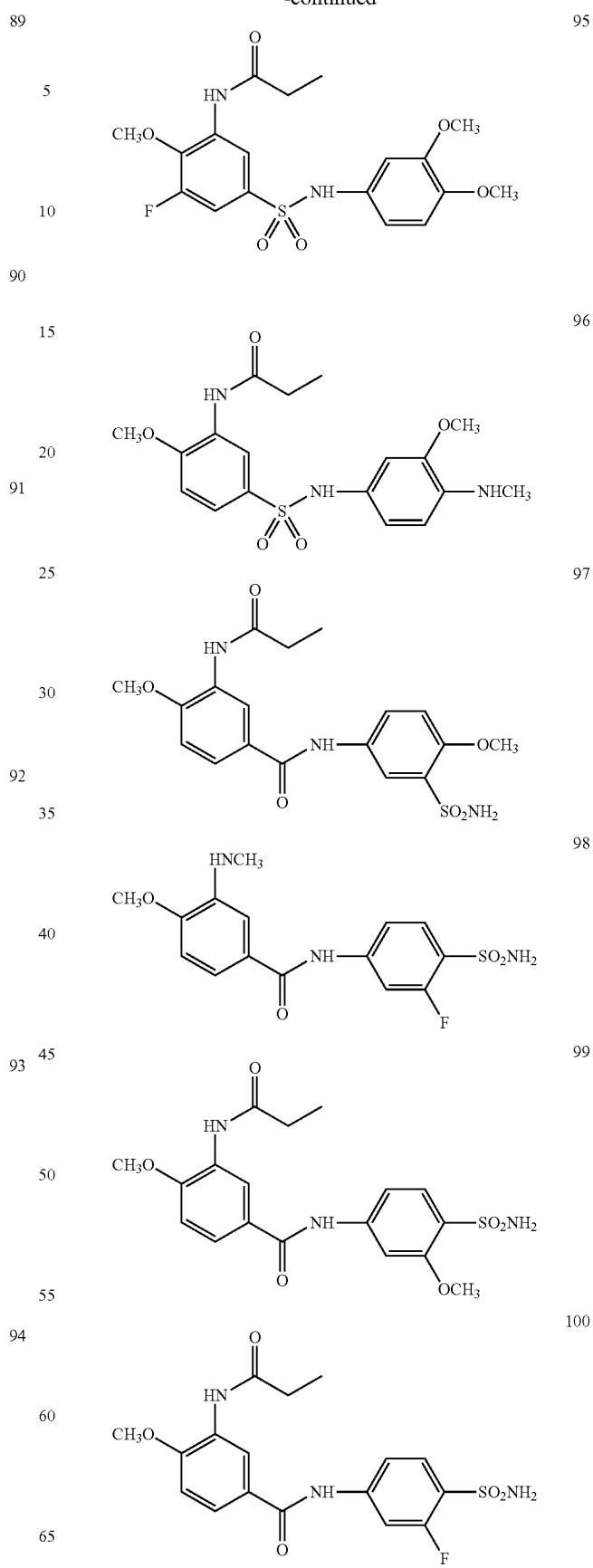

-continued
101
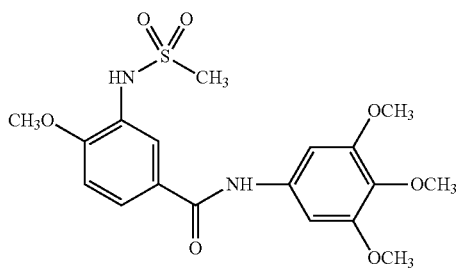
102
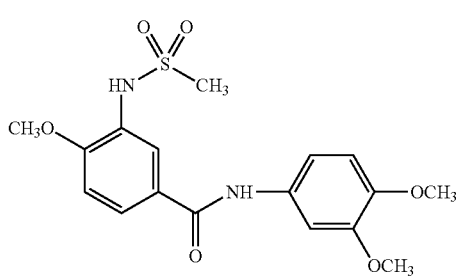
103
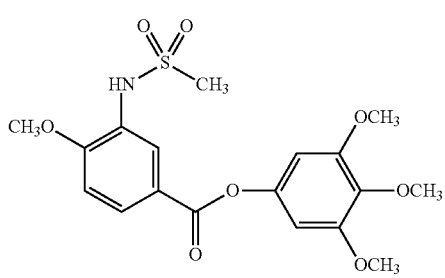
104
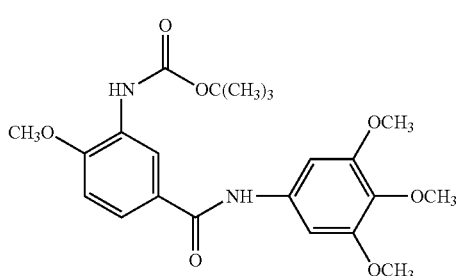
263
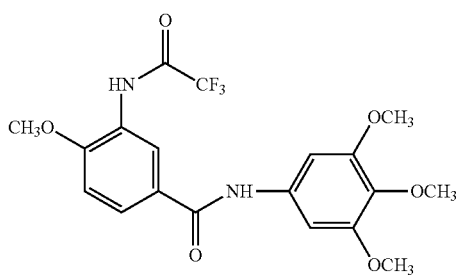
-continued
353
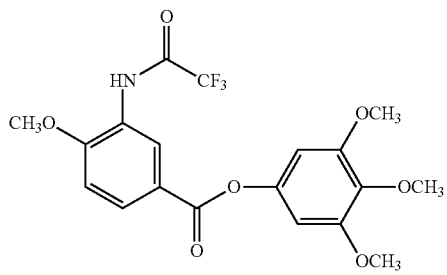
352
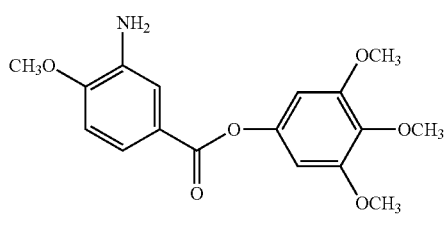
2612
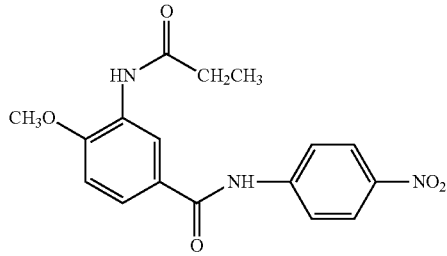
2613
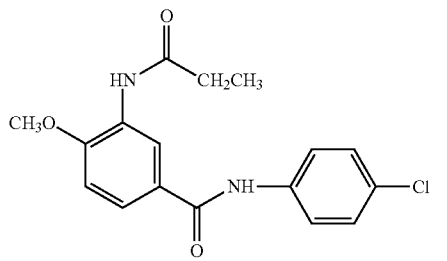
2611
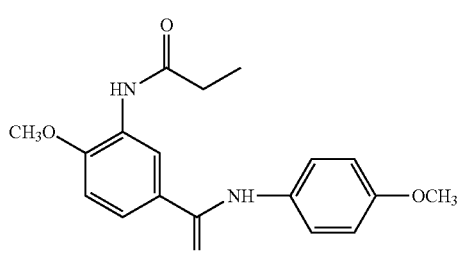
2621
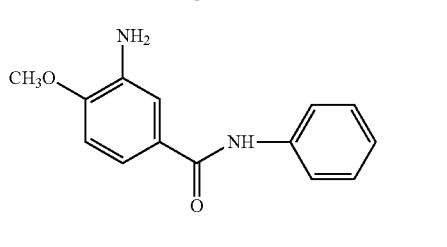
This invention further provides the application of said 3-amino benzoyl derivatives and their salts as hA3G/Vif conjugation inhibitor, as well as their application in the preparation of anti-virus drugs.
Besides, this invention provides anti-virus drug compositions, which contain pharmaceutically effective amounts of said 3-amino benzoyl derivatives or their pharmaceutical salts, mixed with pharmaceutically acceptable adjuvants, diluters etc. The compositions can orally be administered in the forms of pills, capsules, granules, powder or syrupy, or non-orally administered in the form of injections.

The aforementioned preparations of 3-amino benzoyl derivatives can be prepared with the pharmaceutically conventional methods. The pharmaceutical adjuvants that can be used include excipients (e.g. saccharide derivatives such as lactose, sucrose, mannitol and sorbitol; starch and starch derivatives such as corn starch, potato starch, dextrin and carboxymethylstarch; cellulose and its derivatives such as crystalline cellulose, hydroxypropylcellulose, carboxymethylcellulose, calcium carboxymethylcellulose, sodium carboxymethylcellulose; acacia; dextran; silicate derivatives such as aluminum magnesium metasilicate; phosphates such as calcium phosphate; carbonates such as calcium carbonate; sulfates such as calcium sulfate, etc.); adhesives (e.g. gelatin, polyvinylpyrrolidone and polyethylene glycol); disintegrating agents (e.g. cellulose derivatives such as sodium carboxymethylcellulose, polyvinylpyrrolidone); lubricants (e.g. talc, calcium stearate, magnesium stearate, spermaceti wax, boric acid, sodium benzoate, leucine etc.), stabilizers (methyl parahydroxybenzoate, propyl parahydroxybenzoate etc.); correctives (e.g. common sweeteners, sour agents and spices etc.); dilutants and solvents for injections (e.g. water, ethanol and glycerol etc.)

In this invention, the starting materials and reactants for the production of the proposed 3-amino benzoyl derivatives and their pharmaceutical salts are determined according to the structures of X and Y in the target compounds. For instance, when X=O, S or NH; Y=carbonyl or sulfonic, various 3-amino benzoyl derivatives can be produced by condensation of different substituted 3-amino benzoic (benzenesulfonic) acids with aromatic amines or phenols.

The embodiment of the processes may be:

Protected or acylated compound A is mixed with HOBT (1-hydroxyl benzotriazole) and DIC (N,N'-diisopropyl carbodiimide) in appropriate proportion, then the mixture is dissolved into DMF (N,N-dimethyl sulfoxide). About 0.5 h after mixing, B is added into the mixture and the resulted mixture is allowed to react for 24 h at room temperature. The product is purified by means of column chromatography.

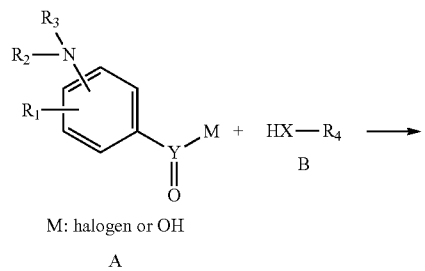

M: halogen or OH

A

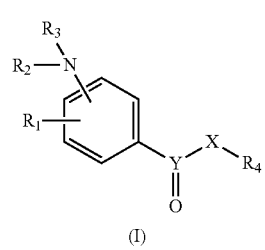

(I)

wherein,
X=O, S or NH;
Y=C, S or SO;
$R_1$, $R_2$, $R_3$ and $R_4$ are the same as above.

In the aforementioned process, the starting material 3-amino benzoic (benzenesulfonic) acids and compound HX—$R_4$ (e.g. aromatic amines, phenols or benzyl alcohols) can be purchased or produced using different known methods.

This invention also provides the test results about pharmaceutical effect researches on said compounds.

Based on the advances making research on the hA3G degradation mediated by HIV-1 Vif, this invention establishes a high throughput anti-HIV-1 drug screening model using hA3G degradation mediated by HIV-1 Vif as target, to screen small molecule active compounds capable of inhibiting this degradation process. The function principle of this model is that HIV-1 Vif protein and hA3G fused yellow fluorescent protein (YFP) co-expressed in the cells, then the intracellular fluorescence intensity (at 530 nm) decreases owing to the degradation of hA3G caused by Vif and subsequent degradation of YEP fused on hA3G. By means of measuring the change of fluorescent intensity, the influence of the screened compounds on the degradation of hA3G caused by Vif can quantitatively be analyzed. Simultaneously, to differentiate the non-specific inhibitory effect of diverse ubiquitin degradation route in the samples, this invention establishes a recheck model based on the detection of P53 degradation caused by the product of adenovirus early gene, to assure that the positive samples screened out by the proposed model can specifically block the degradation of hA3G caused by Vif. The results are shown in Table 1.

The inhibitory activities of the compounds proposed in this invention to HIV-1 were measured using HIV-1 P24 antigen kit. The results are shown in Table 2.

TABLE 1

| \multicolumn{3}{l}{the up-regulation activity of the compounds in this invention to hA3G} | | |
|---|---|---|
| No. of the compounds | Molecular formula and molecular weight | hA3G up-regulation activity (%) |
| 1 | $C_{19}H_{21}ClN_2O_6$ 408.83 | 36.3 |
| 262 | $C_{17}H_{20}N_2O_5$ 332.35 | 36.2 |
| 3 | $C_{15}H_{18}N_4O_4$ 318.33 | 20.2 |
| 4 | $C_{17}H_{19}NO_6$ 333.34 | 1.6 |
| 5 | $C_{17}H_{19}NO_5S$ 349.4 | 14.4 |
| 6 | $C_{18}H_{21}NO_5$ 331.36 | 28.7 |
| 261 | $C_{20}H_{24}N_2O_6$ 388.41 | 43.9 |
| 351 | $C_{20}H_{23}NO_7$ 389.4 | 36.7 |
| 352 | $C_{22}H_{27}NO_8$ 433.45 | 37.0 |
| 353 | $C_{19}H_{18}F_3NO_7$ 429.34 | 39.0 |
| 9 | $C_{20}H_{23}NO_6S$ 405.46 | 46.5 |
| 10 | $C_{21}H_{25}NO_6$ 387.43 | 28.9 |
| 11 | $C_{19}H_{22}N_2O_6$ 374.39 | 22.2 |
| 12 | $C_{19}H_{21}NO_7$ 375.37 | 31.6 |
| 13 | $C_{20}H_{23}NO_6$ 373.4 | 42.1 |

TABLE 1-continued the up-regulation activity of the compounds in this invention to hA3G

| No. of the compounds | Molecular formula and molecular weight | hA3G up-regulation activity (%) |
|---|---|---|
| 14 | $C_{20}H_{23}ClN_2O_6$ 422.86 | 11.2 |
| 15 | $C_{20}H_{22}ClNO_6S$ 439.91 | 19.4 |
| 16 | $C_{21}H_{24}ClNO_6$ 421.87 | 17.3 |
| 17 | $C_{19}H_{21}FN_2O_6$ 392.38 | 31.1 |
| 18 | $C_{19}H_{20}FNO_7$ 393.36 | 34.5 |
| 19 | $C_{19}H_{20}FNO_6S$ 409.43 | 44.3 |
| 20 | $C_{20}H_{22}FNO_6$ 391.39 | 56.0 |
| 21 | $C_{20}H_{22}FNO_6S$ 423.46 | 21.1 |
| 22 | $C_{19}H_{21}NO_6S$ 391.44 | 24.6 |
| 23 | $C_{20}H_{23}FN_2O_6$ 406.4 | 29.3 |
| 24 | $C_{20}H_{22}FNO_7$ 407.39 | 18.6 |
| 25 | $C_{21}H_{24}FNO_6$ 405.42 | 19.4 |
| 26 | $C_{20}H_{23}BrN_2O_6$ 467.31 | 42.7 |
| 2612 | $C_{17}H_{17}N_3O_5$ 343.33 | 22.3 |
| 27 | $C_{19}H_{20}ClNO_7$ 409.82 | 32.1 |
| 28 | $C_{20}H_{22}ClNO_6$ 407.84 | 33.6 |
| 29 | $C_{19}H_{21}BrN_2O_6$ 453.28 | 25.3 |
| 30 | $C_{19}H_{20}BrNO_7$ 454.27 | 15.2 |
| 31 | $C_{21}H_{25}BrN_2O_6$ 481.34 | 26.4 |
| 32 | $C_{21}H_{27}NO_6$ 389.44 | 17.6 |
| 33 | $C_{17}H_{20}N_4O_5$ 360.36 | 21.5 |
| 34 | $C_{17}H_{20}N_2O_5$ 332.35 | 38.3 |
| 35 | $C_{20}H_{22}BrNO_7$ 468.3 | 44.9 |
| 36 | $C_{18}H_{22}N_2O_4$ 330.38 | 8.6 |
| 37 | $C_{17}H_{20}N_2O_3$ 300.35 | 7.7 |
| 38 | $C_{20}H_{25}NO_5$ 359.42 | 17.4 |
| 40 | $C_{17}H_{20}N_2O_4$ 316.35 | 12.7 |
| 41 | $C_{18}H_{22}N_2O_4$ 330.38 | 21.8 |
| 42 | $C_{17}H_{20}N_2O_3$ 300.35 | 34.3 |
| 43 | $C_{18}H_{22}N_2O_3$ 314.38 | 26.4 |
| 45 | $C_{18}H_{24}N_2O_4$ 332.39 | 27.6 |
| 46 | $C_{18}H_{20}N_2O_4$ 328.36 | 29.1 |
| 47 | $C_{16}H_{18}N_4O_4$ 330.34 | 18.2 |
| 48 | $C_{16}H_{18}N_2O_5$ 318.32 | 16.4 |
| 49 | $C_{16}H_{19}N_3O_4$ 317.34 | 9.8 |
| 50 | $C_{17}H_{18}N_2O_4$ 314.34 | −3.1 |
| 51 | $C_{16}H_{17}N_3O_4$ 315.32 | 0.9 |
| 52 | $C_{20}H_{23}FN_2O_6$ 406.4 | 10.1 |
| 53 | $C_{18}H_{19}FN_2O_4$ 346.35 | 13.3 |
| 54 | $C_{16}H_{18}N_2O_3$ 286.33 | 28.7 |
| 55 | $C_{15}H_{16}N_2O_3$ 272.3 | 35.5 |
| 56 | $C_{15}H_{16}N_2O_2$ 256.3 | 41.1 |
| 57 | $C_{19}H_{22}N_2O_4$ 342.39 | 24.0 |
| 58 | $C_{19}H_{22}N_2O_6$ 374.39 | 16.6 |
| 59 | $C_{20}H_{24}N_2O_6$ 388.41 | 19.8 |
| 60 | $C_{17}H_{18}N_2O_3$ 298.34 | 16.3 |
| 61 | $C_{15}H_{16}N_4O_3$ 300.31 | 11.8 |
| 62 | $C_{20}H_{23}NO_7$ 389.4 | 40.1 |
| 63 | $C_{20}H_{24}N_2O_6$ 388.41 | 21.3 |
| 64 | $C_{20}H_{24}N_2O_6$ 388.41 | 11.7 |
| 67 | $C_{18}H_{17}F_3N_2O_4$ 382.33 | 11.3 |
| 68 | $C_{18}H_{18}N_2O_5$ 342.35 | 9.8 |
| 69 | $C_{18}H_{17}F_3N_2O_3$ 366.33 | 31.2 |
| 70 | $C_{17}H_{14}F_4N_2O_3$ 370.3 | 24.7 |
| 71 | $C_{18}H_{19}ClN_2O_5$ 378.81 | 30.1 |
| 72 | $C_{18}H_{18}ClNO_6$ 379.79 | 24.3 |
| 73 | $C_{19}H_{18}F_3NO_6$ 413.34 | 29.0 |
| 74 | $C_{19}H_{19}F_3N_2O_5$ 412.36 | 8.5 |
| 75 | $C_{20}H_{23}FN_2O_6$ 406.4 | −1.1 |
| 76 | $C_{20}H_{21}F_3N_2O_5$ 426.39 | 16.7 |
| 77 | $C_{20}H_{23}FN_2O_6$ 406.4 | 14.9 |
| 78 | $C_{18}H_{19}FN_2O_4$ 346.35 | 8.8 |
| 79 | $C_{20}H_{23}FN_2O_6$ 406.4 | 21.6 |
| 80 | $C_{17}H_{18}FN_3O_3$ 331.34 | 37.1 |
| 81 | $C_{20}H_{25}N_3O_5$ 387.43 | 14.4 |
| 82 | $C_{19}H_{24}N_2O_6S$ 408.47 | 28.5 |
| 83 | $C_{19}H_{24}N_2O_7S$ 424.47 | 31.0 |
| 84 | $C_{19}H_{23}NO_8S$ 425.45 | 9.0 |
| 85 | $C_{16}H_{20}N_2O_6S$ 368.4 | 6.8 |
| 86 | $C_{20}H_{23}NO_7$ 389.4 | 20.3 |
| 87 | $C_{17}H_{19}NO_6$ 333.34 | 19.7 |
| 88 | $C_{19}H_{22}N_2O_6$ 374.39 | 24.8 |
| 89 | $C_{19}H_{25}N_3O_5$ 375.42 | 31.3 |
| 90 | $C_{16}H_{19}NO_7S$ 369.39 | 28.2 |

TABLE 1-continued the up-regulation activity of the compounds in this invention to hA3G

| No. of the compounds | Molecular formula and molecular weight | hA3G up-regulation activity (%) |
|---|---|---|
| 91 | $C_{19}H_{24}N_2O_7S$ 424.47 | 16.6 |
| 92 | $C_{16}H_{20}N_4O_6S$ 396.42 | 23.7 |
| 93 | $C_{16}H_{20}N_4O_6S$ 396.42 | 34.2 |
| 94 | $C_{18}H_{22}N_2O_6S$ 394.44 | 16.1 |
| 95 | $C_{18}H_{21}FN_2O_6S$ 412.43 | 8.7 |
| 96 | $C_{18}H_{23}N_3O_5S$ 393.46 | 6.9 |
| 97 | $C_{18}H_{21}N_3O_6S$ 407.44 | 6.4 |
| 98 | $C_{15}H_{16}FN_3O_4S$ 353.37 | 5.8 |
| 99 | $C_{18}H_{21}N_3O_6S$ 407.44 | 23.6 |
| 100 | $C_{17}H_{18}FN_3O_5S$ 395.41 | 13.6 |
| 101 | $C_{18}H_{22}N_2O_7S$ 410.44 | 22.1 |
| 102 | $C_{17}H_{20}N_2O_6S$ 380.42 | 10.3 |
| 103 | $C_{18}H_{21}NO_8S$ 411.43 | 26.1 |
| 2611 | $C_{18}H_{20}N_2O_4$ 328.36 | 28.9 |
| 2613 | $C_{17}H_{17}ClN_2O_3$ 332.78 | 27.8 |
| 2621 | $C_{15}H_{16}N_2O_3$ 272.3 | 36.2 |
| 263 | $C_{19}H_{19}F_3N_2O_6$ 428.36 | 24.4 |

TABLE 2 inhibitory activity of the compounds in the invention to HIV-1

| compounds | $IC_{50}$ (µg/ml) |
|---|---|
| 26 | 0.0203 |
| 261 | 0.0227 |
| 262 | 0.0244 |
| 263 | <0.0137 |
| 2611 | 0.017☐ |
| 2613 | 0.0138 |
| 2621 | <0.0137 |
| 35 | 0.0223 |
| 351 | 0.0299 |
| 352 | 0.0554 |
| AZT | $5.78 \times 10^{-5}$ |

The above results preliminarily validated the inhibitory effect of the compounds and their pharmaceutically salts according to this invention on the conjugation of hA3G/Vif, as well as their anti-virus effect. These lay the foundation for the development and application of anti-virus drugs.

DETAILED DESCRIPTION OF THE EMBODIMENTS

Examples

By way of the following examples which follow, the technicians in this specialty are expected to understand this invention more comprehensively, however, none of which are intended to limit the scope of the invention.

Example 1

Synthesis of N-(3',4',5'-trimethoxyphenyl) 3-propionamido-4-methoxybenzamide (261)

0.6 g 3-amino-4-methoxybenzoic acid (1.0 g, 6 mmol) is dissolved in dry THF (tetrahydrofuran) in a 25 ml flask, triethylamine (1.2 ml, 12 mmol) is subsequently added to obtain transparent yellow solution. The mixture is stirred under nitrogen protection, propionyl chloride (0.78 ml, 9 mmol) is added into the flask in an ice-water bath. After finishing addition of propionyl chloride the mixture is naturally raised to room temperature. The reacted mixture is filtered, the filtrate is evaporated to dryness and separated using a silica column to obtain 3-propionamido-4-methoxybenzoic acid 1.3 g (yield: 67%).

100 mg of the aforementioned product is mixed with 53 mg (mmol) HOBT and 0.03 ml (mmol) DIC, dissolved into dry DMF in a flask in ice-water bath. The mixture is stirred for 30 min under $N_2$ protection, 72 mg 3,4,5-trimethoxyaniline (mmol) is subsequently added, then the mixture is naturally raised to room temperature and stirred overnight. The reacted mixture is evaporated to dryness and the residue is dissolved into ethyl acetate and subsequently filtered, the filtrate is evaporated to dryness and separated using a preparatory thin layer silica plate to obtain 40 mg compound 261 (yield: 30%).

$^1$H NMR (CDCl$_3$, δ) 1.3 (t, 3H, CH$_3$), 2.5 (q, 2H, CH$_2$), 3.82 (s, 3H, 4'-OCH$_3$), 3.9 (s, 6H, 3',5'-OCH$_3$), 3.95 (s, 3H, 4-OCH$_3$), 6.98 (s, 2H, 2',6'-H), 7.0 (d, 1H, 5-H), 7.8 (dd, 1H, 6-H), 7.9 (br, 2H, NH), 8.9 (d, 1H, 2-H)

Example 2

Synthesis of 3',4',5'-trimethoxyphenyl 3-propionamido-4-methoxybenzoate (351)

Compound 351 is synthesized following a similar method as in Example 1 and using 3-amino-4-methoxy benzoic acid, propionyl chloride and 3,4,5-trimethoxy phenol as materials. Total yield of the two steps: 30%.

$^1$H NMR (CDCl$_3$, δ) 1.3 (t, 3H, CH$_3$), 2.5 (q, 2H, CH$_2$), 3.8 (s, 9H, 4',5',6'-OCH$_3$), 3.95 (s, 3H, 4-OCH$_3$), 6.44 (s, 2H, 2',6'-H), 6.98 (d, 1H, 5-H), 7.76 (br, 1H, 3-NHCO), 7.9 (dd, 1H, 6-H), 7.9 (br, 1H, 1-CONH), 9.2 (d, 1H, 2-H)

Example 3

Synthesis of N-(3',4',5'-trimethoxyphenyl)-3-trifluoroacetamido-4-methoxybenzamide (263)

Compound 263 is synthesized following a similar method as in Example 1 and using 3-amino-4-methoxy benzoic acid, trifluoroacetyl chloride and 3,4,5-trimethoxyaniline as materials. Total yield of the two steps: 50%.

$^1$H NMR (CDCl$_3$, δ) 3.84 (s, 9H, 4',5',6'-OCH$_3$), 4.0 (s, 3H, 4-OCH$_3$), 6.97 (s, 2H, 2',6'-H), 7.03 (d, 1H, 5-H), 7.86 (d, 1H, 6-H), 7.9 (s, 1H, 3-NHCOR), 8.6 (s, 1H, 1-CONH), 8.75 (s, 1H, 2-H)

Example 4

Synthesis of 3,4,5-trimethoxyphenyl 3-trifluoroacetamido-4-methoxybenzoate (353)

Compound 353 is synthesized following a similar method as in Example 1 and using 3-amino-4-methoxy benzoic acid, trifluoroacetyl chloride and 3,4,5-trimethoxyphenol as materials. Total yield of the two steps: 40%.
¹H NMR (CDCl₃, δ) 3.85 (s, 9H, 4',5',6'-OCH₃), 4.0 (s, 3H, 4-OCH₃), 6.46 (s, 2H, 2',6'-H), 7.05 (d, 1H, 5-H), 8.07 (dd, 1H, 6-H), 8.54 (s, 1H, 3-NHCOR), 9.12 (s, 1H, 2-H)

Example 5

Synthesis of N-(4'-chlorophenyl)-3-propionamido-4-methoxybenzamide (2613)

Compound 2613 is synthesized following a similar method as in Example 1 and using 3-amino-4-methoxybenzoic acid, propionyl chloride and 4-chloroaniline as materials. Total yield of the two steps: 30%.
¹H NMR (CDCl₃, δ) 1.28 (t, 3H, CH₃), 2.48 (q, 2H, CH₂), 3.96 (s, 3H, 4'-OCH₃), 6.98 (d, 1H, 5-H), 7.33 (d, 2H, 2',6'-H), 7.6 (d, 2H, 3',5'-H), 7.77 (dd, 1H, 6-H), 7.8 (s, 1H, 3-NHCOR), 8.0 (br, 1H, 1-CONH), 8.87 (s, 1H, 2-H)

Example 6

Synthesis of N-(4'-methoxyphenyl)-3-propionamido-4-methoxybenzamide (2611)

Compound 2611 is synthesized following a similar method as in Example 1 and using 3-amino-4-methoxybenzoic acid, propionyl chloride and 4-methoxyaniline as materials. Total yield of the two steps: 70%.
¹H NMR (DMSO-d6, δ) 1.07 (t, 3H, CH₃), 2.4 (q, 2H, CH₂), 3.73 (s, 3H, 4'-OCH₃), 3.89 (s, 3H, 4-OCH₃), 6.89 (d, 2H, 2',6'-H), 7.1 (d, 1H, 5-H), 7.6 (d, 2H, 3',5'-H), 7.7 (dd, 1H, 6-H), 8.48 (br, 1H, 3-NHCOR), 9.15 (s, 1H, 2-H), 10.0 (s, 1H, 1-CONH)

Example 7

Synthesis of N-(3',4',5'-trimethoxyphenyl)-3-(2-chloroacetamido)-4-methoxybenzamide (1)

Compound 1 is synthesized following a similar method as in Example 1 and using 3-amino-4-methoxybenzoic acid, 2-chloroacetyl chloride and 3,4,5-trimethoxyaniline as materials. Total yield of the two steps: 56%.
¹H NMR (CDCl₃, δ) 4.5 (s, 2H, CH₂), 3.82 (s, 3H, 4'-OCH₃), 3.9 (s, 6H, 3',5'-OCH₃), 3.95 (s, 3H, 4-OCH₃), 6.98 (s, 2H, 2',6'-H), 7.0 (d, 1H, 5-H), 7.8 (dd, 1H, 6-H), 7.9 (br, 2H, NH), 8.9 (d, 1H, 2-H)

Example 8

Synthesis of S-(3',4',5'-trimethoxyphenyl) 3-propionamido-4-methoxybenzenecarbothiolate (9)

Compound 9 is synthesized following a similar method as in Example 1 and using 3-amino-4-methoxybenzoic acid, propionyl chloride and 3,4,5-trimethoxythiophenol as materials. Total yield of the two steps: 50%.
¹H NMR (CDCl₃, δ) 1.3 (t, 3H, CH₃), 2.5 (q, 2H, CH₂), 3.8 (s, 9H, 4',5',6'-OCH₃), 3.95 (s, 3H, 4-OCH₃), 6.44 (s, 2H, 2',6'-H), 6.98 (d, 1H, 5-H), 7.76 (br, 1H, NH), 7.9 (dd, 1H, 6-H), 7.9 (br, 2H, NH), 9.2 (d, 1H, 2-H)

Example 9

S-(3',4',5'-trimethoxyphenyl)-3-(2-fluoropropionamido)-4-methoxybenzenecarbothiolate (21)

Compound 21 is synthesized following a similar method as in Example 1 and using 3-amino-4-methoxybenzoic acid, 2-fluoropropionyl chloride and 3,4,5-trimethoxythiophenol as materials. Total yield of the two steps: 54%.
¹H NMR (CDCl₃, δ) 1.3 (d, 3H, CH₃), 4.5 (q, 1H, CH), 3.8 (s, 9H, 4',5',6'-OCH₃), 3.95 (s, 3H, 4-OCH₃), 6.44 (s, 2H, 2',6'-H), 6.98 (d, 1H, 5-H), 7.76 (br, 1H, NH), 7.9 (dd, 1H, 6-H), 7.9 (br, 2H, NH), 9.2 (d, 1H, 2-H)

Example 10

Synthesis of N-(3',4',5'-trimethoxyphenyl)-3-methoxy-4-propionamidobenzamide (64)

Compound 64 is synthesized following a similar method as in Example 1 and using 3-methoxy-4-aminobenzoic acid, propionyl chloride and 3,4,5-trimethoxyaniline as materials. Total yield of the two steps: 57%.
¹H NMR (CDCl₃) δ 1.3 (t, 3H, CH₃), 2.5 (q, 2H, CH₂), 3.82 (s, 3H, 4'-OCH₃), 3.9 (s, 6H, 3',5'-OCH₃), 3.95 (s, 3H, 4-OCH₃), 6.98 (s, 2H, 2',6'-H), 7.0 (d, 1H, 2-H), 7.8 (dd, 1H, 6-H), 7.9 (br, 2H, NH), 8.0 (d, 1H, 5-H)

Example 11

Synthesis of N-(4'-methoxyfuryl-2'-)-4-methoxy-3-propionamidobenzamide (48)

Compound 48 is synthesized following a similar method as in Example 1 and using 3-amino-4-methoxybenzoic acid, propionyl chloride and 2-amino-4-methoxyfuran as materials. Total yield of the two steps: 70%.
¹H NMR (DMSO-d6, δ) 1.07 (t, 3H, CH₃), 2.4 (q, 2H, CH₂), 3.89 (s, 3H, 4-OCH₃), 4.73 (s, 3H, 4'-OCH₃), 6.89 (s, 1H, 5'-H), 7.6 (d, 1H, 5-H), 7.7 (dd, 1H, 6-H), 7.89 (s, 1H, 3'-H), 8.48 (br, 1H, 3-NHCOR), 9.15 (s, 1H, 2-H), 10.0 (s, 1H, 1-CONH)

Example 12

Synthesis of N-(4'-methoxypyrryl-2'-)-4-methoxy-3-propionamidobenzamide (49)

Compound 49 is synthesized following a similar method as in Example 1 and using 3-amino-4-methoxybenzoic acid, propionyl chloride and 2-amino-4-methoxypyrrole as materials. Total yield of the two steps: 68%.
¹H NMR (DMSO-d6, δ) 1.07 (t, 3H, CH₃), 2.4 (q, 2H, CH₂), 3.89 (s, 3H, 4-OCH₃), 4.73 (s, 3H, 4'-OCH₃), 6.76 (s, 1H, 5'-H), 7.6 (d, 1H, 5-H), 7.7 (dd, 1H, 6-H), 7.72 (s, 1H, 3'-H), 8.48 (br, 1H, 3-NHCOR), 9.15 (s, 1H, 2-H), 10.0 (s, 1H, 1-CONH)

Example 13

Synthesis of N-(pyrimidyl-4'-)-4-methoxy-3-propionamidobenzamide (61)

Compound 49 is synthesized following a similar method as in Example 1 and using 3-amino-4-methoxybenzoic acid, propionyl chloride and 4-aminopyrimidine as materials. Total yield of the two steps: 47%.
¹H NMR (DMSO-d6, δ) 1.07 (t, 3H, CH₃), 2.4 (q, 2H, CH₂), 3.89 (s, 3H, 4-OCH₃), 6.76 (d, 1H, 5'-H), 7.2 (d, 1H, 5-H), 7.6 (d, 1H, 5-H), 7.7 (dd, 1H, 6-H), 8.2 (s, 1H, 3'-H), 8.48 (br, 1H, 3-NHCOR), 9.15 (s, 1H, 2-H), 10.0 (s, 1H, 1-CONH)

Example 14

Synthesis of N-(3',4',5'-trimethoxyphenyl)-2-propionamido-4-methoxybenzamide (63)

Compound 63 is synthesized following a similar method as in Example 1 and using 2-amino-4-methoxybenzoic acid, propionyl chloride and 3,4,5-trimethoxyaniline as materials. Total yield of the two steps: 64%.

$^1$H NMR (CDCl$_3$, δ) 1.3 (t, 3H, CH$_3$), 2.5 (q, 2H, CH$_2$), 3.82 (s, 3H, 4'-OCH$_3$), 3.9 (s, 6H, 3',5'-OCH$_3$), 3.95 (s, 3H, 4-OCH$_3$), 6.98 (s, 2H, 2',6'-H), 7.0 (d, 1H, 3-H), 7.8 (dd, 1H, 6-H), 7.9 (br, 2H, NH), 8.0 (d, 1H, 5-H)

Example 15

Synthesis of N-(4'-trifluoromethoxyphenyl)-3-propionamido-4-methylbenzamide (69)

Compound 69 is synthesized following a similar method as in Example 1 and using 3-amino-4-methylbenzoic acid, propionyl chloride and 4-trifluoromethoxyaniline as materials. Total yield of the two steps: 49%.

$^1$H NMR (DMSO-d6, δ) 1.07 (t, 3H, CH$_3$), 2.4 (q, 2H, CH$_2$), 2.5 (s, 3H, 4-CH$_3$), 3.89 (s, 3H, 4-OCH$_3$), 6.89 (d, 2H, 2',6'-H), 7.1 (d, 1H, 5-H), 7.6 (d, 2H, 3',5'-H), 7.7 (dd, 1H, 6-H), 8.48 (br, 1H, 3-NHCOR), 9.15 (s, 1H, 2-H), 10.0 (s, 1H, 1-CONH)

Example 16

Synthesis of 3',4',5'-trimethoxyphenyl 3-acetamido-5-trifluoromethylbenzoate (73)

Compound 73 is synthesized following a similar method as in Example 1 and using, 3-amino-5-trifluoromethylbenzoic acid, acetyl chloride and 3,4,5-trimethoxyphenol materials. Total yield of the two steps: 61%.

$^1$H NMR (CDCl$_3$, δ) 2.3 (s, 3H, CH$_3$), 3.8 (s, 9H, 4',5',6'-OCH$_3$), 6.44 (s, 2H, 2',6'-H), 6.98 (d, 1H, 5-H), 7.76 (br, 1H, NH), 7.9 (dd, 1H, 6-H), 7.9 (br, 2H, NH), 9.2 (d, 1H, 2-H)

Example 17

Synthesis of N-(3',4',5'-trimethoxyphenyl)-3-propionamido-4-fluoro-5-methoxybenzamide (75)

Compound 75 is synthesized following a similar method as in Example 1 and using 3-amino-4-fluoro-5-methoxybenzoic acid, propionyl chloride and 3,4,5-trimethoxyaniline as materials. Total yield of the two steps: 76%.

$^1$H NMR (CDCl$_3$, δ) 2.3 (s, 3H, CH$_3$), 3.8 (s, 9H, 4',5',6'-OCH$_3$), 3.97 (s, 3H, 5-OCH$_3$), 6.44 (s, 2H, 2',6'-H), 7.76 (br, 1H, NH), 7.9 (d, 1H, 6-H), 7.9 (br, 1H, NH), 9.2 (d, 1H, 2-H)

Example 18

Synthesis of N-(3',4',5'-trimethoxyphenyl)-3-propionamido-4-methoxy-6-fluorobenzamide (79)

Compound 79 is synthesized following a similar method as in Example 1 and using 3-amino-4-methoxy-6-fluorobenzoic acid, propionyl chloride and 3,4,5-trimethoxyaniline as materials. Total yield of the two steps: 66%.

$^1$H NMR (CDCl$_3$, δ) 1.07 (t, 3H, CH$_3$), 2.3 (q, 2H, CH$_2$), 3.8 (s, 9H, 4',5',6'-OCH$_3$), 3.97 (s, 3H, 4-OCH$_3$), 6.44 (s, 2H, 2',6'-H), 7.76 (br, 1H, NH), 7.9 (s, 1H, 5-H), 7.9 (br, 1H, NH), 9.2 (s, 1H, 2-H)

Example 19

Synthesis of N-(3'-fluoro-4'-aminophenyl)-3-propionamido-4-methoxybenzamide (80)

Compound 80 is synthesized following a similar method as in Example 1 and using 3-amino-4-methoxybenzoic acid, propionyl chloride and 3-fluoro-4-aminoaniline as materials. Total yield of the two steps: 60%.

$^1$H NMR (CDCl$_3$, δ) 1.07 (t, 3H, CH$_3$), 2.4 (q, 2H, CH$_2$), 3.89 (s, 3H, 4-OCH$_3$), 6.89 (d, 2H, 2',6'-H), 7.1 (d, 1H, 5-H), 7.6 (d, 1H, 5'-H), 7.7 (dd, 1H, 6-H), 8.3 (d, 1H, 6'-H), 8.48 (br, 1H, 3-NHCOR), 9.15 (s, 1H, 2-H), 9.3 (s, 1H, 2'-H), 10.0 (s, 1H, 1-CONH)

Example 20

Synthesis of N-(3',4',5'-trimethoxyphenyl) 3-propionamido-4-methoxybenzenesulfamide (83)

Compound 83 is synthesized following a similar method as in Example 1 and using 3-amino-4-methoxybenzenesulfonic acid, propionyl chloride and 3,4,5-trimethoxyaniline as materials. Total yield of the two steps: 63%.

$^1$H NMR (DMSO-d6, δ) 1.03 (t, 3H, CH$_3$), 2.5 (q, 2H, CH$_2$), 3.8 (s, 9H, 4',5',6'-OCH$_3$), 3.95 (s, 3H, 4-OCH$_3$), 6.7 (s, 2H, 2',6'-H), 7.3 (d, 1H, 5-H), 7.7 (br, 1H, CONH) 7.9 (dd, 1H, 6-H), 8.8 (br, 1H, SO2NH), 9.2 (d, 1H, 2-H).

Example 21

Synthesis of 3',4',5'-trimethoxyphenyl 3-propionamido-4-methoxybenzenesulfonate (84)

Compound 84 is synthesized following a similar method as in Example 1 and using 3-amino-4-methoxybenzenesulfonic acid, propionyl chloride and 3,4,5-trimethoxyphenol as materials. Total yield of the two steps: 53%.

$^1$H NMR (CDCl$_3$, δ) 1.03 (t, 3H, CH$_3$), 2.5 (q, 2H, CH$_2$), 3.8 (s, 9H, 4',5',6'-OCH$_3$), 3.95 (s, 3H, 4-OCH$_3$), 6.7 (s, 2H, 2',6'-H), 7.3 (d, 1H, 5-H), 7.7 (br, 1H, CONH) 7.9 (dd, 1H, 6-H), 9.2 (d, 1H, 2-H)

Example 22

Synthesis of N-(3'-propionamido-4'-methoxyphenyl)-(3,4,5-trimethoxy)benzenesulfonamide (91)

Compound 91 is synthesized following a similar method as in Example 1 and using 3-propionamido-4-methoxyaniline and 3,4,5-trimethoxybenzenesulfonic acid as materials. Total yield of the two steps: 40%.

$^1$H NMR (DMSO-d6, δ) 1.03 (t, 3H, CH$_3$), 2.5 (q, 2H, CH$_2$), 3.8 (s, 9H, 3',4',5'-OCH$_3$), 3.95 (s, 3H, 4-OCH$_3$), 6.3 (d, 1H, 6-H), 6.7 (br, 1H, CONH) 6.9 (dd, 1H, 5-H), 7.7 (s, 2H, 2',6'-H), 8.8 (br, 1H, SO2NH), 9.2 (d, 1H, 2-H)

Example 23

Synthesis of 3',4',5'-trimethoxyphenyl 3-methanesulfamido-4-methoxybenzoate (103)

Compound 103 is synthesized following a similar method as in Example 1 and using 3-amino-4-methoxybenzoic acid, methanesulfonyl chloride and 3,4,5-trimethoxyphenol as materials. Total yield of the two steps: 52%.

$^1$H NMR (DMSO-d6, δ) 2.5 (s, 3H, CH$_3$), 3.8 (s, 9H, 3',4',5'-OCH$_3$), 3.95 (s, 3H, 4-OCH$_3$), 6.7 (s, 2H, 2',6'-H), 7.3 (d, 1H, 5-H), 7.7 (br, 1H, CONH) 7.9 (dd, 1H, 6-H), 9.2 (d, 1H, 2-H)

Example 24

Synthesis of 3',4',5'-trimethoxyphenyl 3-trifluoroacetamido-4-methoxybenzoate (103)

Compound 353 is synthesized following a similar method as in Example 1 and using 3-amino-4-methoxybenzoic acid, trifluoroacetyl chloride and 3,4,5-trimethoxyphenol as materials. Total yield of the two steps: 46%.

$^1$H NMR (CDCl$_3$, δ) 3.8 (s, 9H, 3',4',5'-OCH$_3$), 6.44 (s, 2H, 2',6'-H), 6.98 (d, 1H, 5-H), 7.76 (br, 1H, NH), 7.9 (dd, 1H, 6-H), 9.2 (d, 1H, 2-H)

Example 25

Synthesis of N-(4'-nitrophenyl)-3-propionamido-4-methoxybenzamide (2612)

Compound 2612 is synthesized following a similar method as in Example 1 and using 3-amino-4-methoxybenzoic acid, propionyl chloride and 4-nitroaniline as materials. Total yield of the two steps: 53%.

$^1$H NMR (DMSO-d1, δ) 1.07 (t, 3H, CH$_3$), 2.4 (q, 2H, CH$_2$), 3.73 (s, 3H, 4'-OCH$_3$), 3.89 (s, 3H, 4-OCH$_3$), 6.89 (d, 2H, 2',6'-H), 7.1 (d, 1H, 5-H), 7.7 (dd, 1H, 6-H), 8.3 (d, 2H, 3',5'-H), 8.48 (br, 1H, 3-NHCOR), 9.15 (s, 1H, 2-H), 10.0 (s, 1H, 1-CONH)

Example 26

Synthesis of N-(4'-chlorophenyl)-3-propionamido-4-methoxybenzamide (2613)

Compound 2613 is synthesized following a similar method as in Example 1 and using 3-amino-4-methoxybenzoic acid, propionyl chloride and 4-chloroaniline as materials. Total yield of the two steps: 56%.

$^1$H NMR (DMSO-d6, δ) 1.07 (t, 3H, CH$_3$), 2.4 (q, 2H, CH$_2$), 3.73 (s, 3H, 4'-OCH$_3$), 3.89 (s, 3H, 4-OCH$_3$), 6.6 (d, 2H, 2',6'-H), 7.1 (d, 1H, 5-H), 7.7 (dd, 1H, 6-H), 8.2 (d, 2H, 3',5'-H), 8.48 (br, 1H, 3-NHCOR), 9.15 (s, 1H, 2-H), 10.0 (s, 1H, 1-CONH)

Example 27

Synthesis of N-(3',4',5'-trimethoxyphenyl)-3-cyano-4-methoxybenzamide (68)

Compound 68 is synthesized following a similar method as in Example 1 and using 3-cyano-4-methoxybenzoic acid and 3,4,5-trimethoxyaniline as materials. Total yield of the two steps: 60%.

$^1$H NMR (CDCl$_3$, δ) 3.82 (s, 3H, 4'-OCH$_3$), 3.9 (s, 6H, 3',5'-OCH$_3$), 3.95 (s, 3H, 4-OCH$_3$), 6.68 (s, 2H, 2',6'-H), 6.8 (d, 1H, 5-H), 7.0 (dd, 1H, 6-H), 7.9 (br, 2H, NH), 8.9 (d, 1H, 2-H)

Following a similar method as in Example 1, compounds 11, 12, 14, 15, 17, 18, 19, 21, 22, 23, 24, 26, 27, 29, 30, 31, 33, 35, 46, 47, 50, 51, 52, 53, 57, 58, 59, 60, 62, 67, 70, 71, 72, 74, 76, 77, 78, 81, 82, 86, 88, 89, 92, 93, 94, 95, 96, 97, 99, 100, 101, 102, 104 are also obtained.

Example 28

Synthesis of N-(3',4',5'-trimethoxyphenyl) 3-amino-4-methoxybenzamide (262)

1) 1.0 g (6 mmol) 3-amino-4-methoxybenzoic acid is dissolved in 10 ml 4N NaOH aqueous solution, 2.5 ml (11 mmol) tert-butyric anhydride is slowly dropped into the solution. The mixture is heated up to 50° C. until the reaction finishes and the resulted alkaline solution is quickly acidified to pH=2 using 1 N hydrochloric acid and extracted three times using chloroform. The chloroform extract is pooled and desiccated with anhydrate sodium sulfate, subsequently condensed to dryness to obtain 0.8 g off-white solid, yield: 50%.

2) 200 mg (0.8 mmol) of the product from step 1) is mixed with 120 mg (0.9 mmol) HOBT and 0.06 ml (0.6 mmol) DIC in dry DMF under ice-water bath condition. The mixture is stirred for 30 min. under N$_2$ protection, then 160 mg (0.9 mmol) 3,4,5-trimethoxyaniline is subsequently added, the mixture is let to naturally resume room temperature and stirred overnight. The resulted reactant is evaporated to dryness under reduced pressure, the residue is dissolved in ethyl acetate and subsequently filtered, the filtrate is evaporated to dryness, separated using preparatory thin layer silica plate to obtain 180 mg product, yield: 55.6%.

3) 160 mg of the product from step 2) is dissolved into 6 ml methanol, 0.12 ml acetyl chloride is dropped into the solution, reacting until all of the tert-butyryl protective group is removed, subsequently, the reactant is evaporated to dryness, the residue is evenly mixed with 10 ml methylene chloride, filtered to obtain 60 mg white solid (262), yield: 49%.

$^1$H NMR (DMSO-d6, δ) 3.62 (s, 3H, 4'-OCH$_3$), 3.78 (s, 6H, 3',5'-OCH$_3$), 3.95 (s, 3H, 4-OCH$_3$), 4.5 (br, 2H, —NH2), 7.1 (d, 1H, 5-H), 7.2 (s, 2H, 2',6'-H), 7.6 (s, 1H, 6-H), 7.7 (s, 1H, 2-H), 10.0 (s, 1H, 1-CONH)

Example 29

Synthesis of 3-amino-4-methoxybenzanilide (2621)

Using 3-amino-4-methoxybenzoic acid and aniline as materials, compound 2621 is synthesized following a similar method as in Example 28. Yield: 37%.

$^1$H NMR (DMSO-d6, δ) 3.55 (s, 3H, 4-OCH$_3$), 4.5 (br, 2H, —NH2), 7.0 (m, 1H, 4'-H), 7.1 (d, 1H, 5-H), 7.2 (d, 2H, 2',6'-H), 7.4 (dd, 2H, 3',5'-H), 7.6 (d, 1H, 6-H), 7.7 (s, 1H, 2-H), 10.0 (s, 1H, 1-CONH)

Example 30

Synthesis of N-(3'-fluoro-4'-aminosulfonylphenyl)-3-methylamino-4-methoxybenzamide (98)

Using 3-methylamino-4-methoxybenzoic acid and 3-fluoro-4-aminosulfonylaniline as materials, compound 98 is synthesized following a similar method as in Example 28. Yield: 52%.

$^1$H NMR (DMSO-d6, δ) 2.5 (br, 2H, —NH2), 2.8 (d, 3H, 3-CH$_3$), 3.75 (s, 3H, 4-OCH$_3$), 4.5 (br, 1H, 3-NH), 6.5 (m, 1H, 6'-H), 6.67 (s, 1H, 2'-H), 6.8 (d, 1H, 5-H), 7.2 (d, 1H, 5'-H), 7.4 (dd, 2H, 3',5'-H), 7.6 (d, 1H, 6-H), 7.7 (s, 1H, 2-H), 10.0 (s, 1H, 1-CONH)

Example 31

Synthesis of N-(2',6'-dimethoxypyrimidinyl-4'-)
3-methylamino-4-hydroxylbenzamide (3)

Using 3-methylamino-4-hydroxylbenzoic acid and 2,6-dimethoxy-4-aminopyrimidine as materials, compound 3 is synthesized following a similar method as in Example 28. Yield: 67%.

$^1$H NMR (DMSO-d6, δ) 2.8 (d, 3H, 3-CH$_3$), 3.73 (s, 3H, 6'-OCH$_3$), 3.77 (s, 3H, 2'-OCH$_3$), 4.4 (br, 1H, 3-NH), 5.1 (br, 1H, 4-OH), 6.8 (d, 1H, 5-H), 7.2 (d, 1H, 5'-H), 7.6 (d, 1H, 6-H), 7.7 (s, 1H, 2-H), 9.2 (s, 1H, 1-CONH)

Example 32

Synthesis of S-(3',4',5'-trimethoxyphenyl) 3-amino-4-methoxybenzenecarbothioate (5)

Using 3-amino-4-methoxybenzoic acid and 3,4,5-trimethoxyphenylmercaptan as materials, compound 5 is synthesized following a similar method as in Example 28. Yield: 47%.

$^1$H NMR (DMSO-d6, δ) 3.62 (s, 3H, 4'-OCH$_3$), 3.78 (s, 6H, 3',5'-OCH$_3$), 3.95 (s, 3H, 4-OCH$_3$), 4.2 (br, 2H, —NH2), 7.1 (d, 1H, 5-H), 7.3 (s, 2H, 2',6'-H), 7.6 (s, 1H, 6-H), 7.7 (s, 1H, 2-H)

Example 33

Synthesis of N-(3',5'-dimethoxyphenyl)-3-methylamino-4-methoxybenzamide (40)

Using 3-methylamino-4-methoxybenzoic acid and 3,5-dimethoxyaniline as materials, compound 40 is synthesized following a similar method as in Example 28. Yield: 50%.

$^1$H NMR (DMSO-d6, δ) 2.4 (d, 3H, 3-CH$_3$), 3.75 (s, 3H, 4-OCH$_3$), 3.8 (s, 6H, 3',5'-OCH$_3$), 5.0 (br, 1H, 3-NH), 6.5 (s, 2H, 2',6'-H), 6.8 (d, 1H, 5-H), 7.6 (d, 1H, 6-H), 7.7 (s, 1H, 2-H), 9.4 (s, 1H, 1-CONH)

Example 34

Synthesis of N-(3',4',5'-trimethoxyphenyl)-3-amino-4-methoxybenzenesulfonamide (85)

Using 3-methylamino-4-methoxybenzoic acid and 3,4,5-trimethoxyaniline as materials, compound 85 is synthesized following a similar method as in Example 28. Yield: 52%.

$^1$H NMR (DMSO-d6) δ 3.62 (s, 9H, 3',4',5'-OCH$_3$), 3.78 (s, 3H, 4-OCH$_3$), 4.2 (br, 2H, —NH2), 7.1 (d, 1H, 5-H), 7.3 (s, 2H, 2',6'-H), 7.6 (s, 1H, 6-H), 7.7 (s, 1H, 2-H), 8.5 (br, 1H, —SO2NH)

Example 35

Synthesis of N-(3',4',5'-trimethoxyphenyl)-3-hydroxyl-4-methoxybenzamide (87)

Using 3-hydroxyl-4-methoxybenzoic acid and 3,4,5-trimethoxyaniline as materials, compound 87 is synthesized following a similar method as in Example 28. Yield: 34%.

$^1$H NMR (DMSO-d6, δ) 3.62 (s, 9H, 3',4',5'-OCH$_3$), 3.78 (s, 3H, 4-OCH$_3$), 5.2 (br, 1H, —OH), 7.1 (d, 1H, 5-H), 7.3 (s, 2H, 2',6'-H), 7.6 (s, 1H, 6-H), 7.7 (s, 1H, 2-H), 8.9 (br, 1H, —CONH)

Example 36

Synthesis of 3',4',5'-trimethoxyphenyl
3-amino-4-methoxybenzoate (352)

Using 3-amino-4-methoxybenzoic acid and 3,4,5-trimethoxyphenol as materials, compound 352 is synthesized following a similar method as in Example 28. Yield: 30%.

$^1$H NMR (DMSO-d6, δ) 3.65 (s, 3H, 4'-OCH$_3$), 3.75 (s, 6H, 3',5'-OCH$_3$), 3.85 (s, 3H, 4-OCH$_3$), 5.05 (br, 2H, —NH2), 6.56 (s, 2H, 2',6'-H), 6.94 (d, 1H, 5-H), 7.35 (d, 1H, 6-H), 7.38 (s, 1H, 2-H)

Following a similar method as in Example 28, compounds 4, 6, 34, 36, 37, 41, 42, 43, 45, 54, 55, 56, 90 are also synthesized.

Example 37

Synthesis of 1'-(3-propionamido-4-methoxy-benzoyl)methylene-3',4',5'-trimethoxybenzene (10)

0.6 g 3-amino-4-methoxybenzoic acid (1.0 g, 6 mmol) is dissolved in dry tetrahydrofuran in a 25 ml flask, triethylamine (1.2 ml, 12 mmol) is added into the solution to obtain a transparent yellow solution. The flask in placed in an ice-water bath, the mixture is stirred under nitrogen protection, propionyl chloride (0.78 ml, 9 mmol) is added drop wise into the mixture. After drop wise addition, the mixture stands at room temperature and is allowed to react. The resulted reactant is subsequently filtered, the filtrate is evaporated to dryness and the residue is separated in a silica column to obtain 1.3 g 3-propionamido-4-methoxybenzoic acid.

1.3 g 3-propionamido-4-methoxybenzoic acid is mixed with 10 ml dichlorosulfoxide and the mixture is stirred for more than 1 h at room temperature. The excessive dichlorosulfoxide is evaporated with additions of toluene in the mixture for several times to ensure thorough removal of dichlorosulfoxide. The residue is dissolved into anhydrous ethyl ether, equivalent amount of 3,4,5-trimethoxybenzyl cadmium is added into the mixture under ice-water cooling and reacted for more than 1 h with the temperature maintained within 0~-5° C. The reaction are carried out under normal Grignard reaction conditions, to obtain 1.2 g target compound (10) (yield: 52%).

$^1$H NMR (CDCl$_3$, δ) 1.03 (t, 3H, CH$_3$), 2.5 (q, 2H, CH$_2$), 3.4 (s, 2H, —COCH$_2$), 3.8 (s, 9H, 4',5',6'-OCH$_3$), 3.95 (s, 3H, 4-OCH$_3$), 6.7 (s, 2H, 2',6'-H), 7.3 (d, 1H, 5-H), 7.4 (s, 1H, 3-NHCO), 7.9 (dd, 1H, 6-H), 8.4 (s, 1H, 1-CONH), 9.2 (s, 1H, 2-H)

Example 38

Synthesis of 3-(2"-fluoropropionamido)-4-methoxy-benzoylmethylene-3',4',5'-trimethoxybenzene (25)

Using 3-hydroxyl-4-methoxybenzoic acid, 2-fluoropropionyl chloride and 3,4,5-tribenzyl cadmium as materials, compound 25 is synthesized following a similar method as in Example 37. Yield: 57%.

¹H NMR (CDCl₃, δ) 1.3 (d, 3H, CH₃), 3.2 (s, 2H, —COCH₂), 3.8 (s, 9H, 4',5',6'-OCH₃), 3.95 (s, 3H, 4-OCH₃), 4.5 (q, 1H, CHF), 6.44 (s, 2H, 2',6'-H), 6.98 (d, 1H, 5-H), 7.16 (br, 1H, 3-NHCO), 7.4 (dd, 1H, 6-H), 7.9 (br, 1H, 1-CONH), 9.2 (d, 1H, 2-H)

Example 39

Synthesis of 1-(3'-propionamido-4'-methoxyphenyl)-2-(3",4",5"-trimethoxyphenyl)ethanol (32)

The product (25) obtained from Example 38 is dissolved into methanol, appropriate amount of NaBH₄ is added to reduce product (25), terminate the reaction when the material is depleted, the mixture is separated to obtain the target compound 32 (yield: 86).

¹H NMR (DMSO-d6, δ) 1.03 (t, 3H, CH₃), 2.5 (q, 2H, CH₂), 3.8 (s, 9H, 4',5',6'-OCH₃), 3.95 (s, 3H, 4-OCH₃), 4.4 (d, 2H, 2-CH₂), 5.0 (t, 1H, 1-CH), 6.7 (s, 2H, 2", 6"-H), 7.3 (d, 1H, 5'-H), 7.4 (s, 1H, 3'-NHCO), 7.9 (dd, 1H, 6'-H), 9.2 (s, 1H, 2'-H)

Following a similar method as in Example 37, compounds 13, 16, 20, 28 are also obtained.

Example 40

Screening Experiment for Up-Regulation Activity to hA3G

The cells are picked up and cultured a culture bottle. When the cells grow full of the culture bottle, old culture medium is discarded and the cells are digested with digestion medium. When the cells turn round, the digestion medium is discarded and the culture medium is added in at once, the bottom of the bottle is gently blown with a pipette to make the cells disengage the bottle bottom and disperse into single cell suspension. After counting the cells using blood cell counting chamber, the cell suspension is inoculated into a culture dish for transfection. The medium containing the plasmid to be transfected and the transfection reagents is gently mixed up and incubated at room temperature. The medium is then added into the supernatant of the cell culture and cultured for a certain period of time. The old culture medium is then sucked out, the cells are digested with digestive medium, the digestive medium is subsequently discarded and culture medium is immediately added. The medium is gently blown to disperse the cells into single cell suspension. After counting the cells using blood cell counting chamber, the cells are ready for inoculation.

Samples of compounds☐Pure tested compounds are dissolved in DMSO, the solution is diluted with equal proportional distilled water. The diluent is used to test the cell systems.

Sample solution of different concentration is added into the supernatant of a cell culture. After the cells are continuously cultured, old culture medium is sucked out and the cells are blown with PBS buffer until the cells completely disengage from the culture bottle.

The fluorescence intensity values of the cell suspension with test compound samples, positive control samples and negative control samples are respectively measured with fluorometer, the excitation wavelength is 485 nm and the detection wavelength 520 nm. Averages of duplicated measurements are taken as the results.

The measured fluorescence intensity values of the negative control samples (blink sample) subtracted from those of test compound samples, the results are taken as YFP fluorescence of different groups.

Relative fluorescence intensity=fluorescence intensity of a test sample group/fluorescence intensity of the positive control group×100%

Inhibition rate of degradation=(test sample group-negative control group)/(positive control group-negative control group)×100%

The results of the screening are shown in Table 1.

Example 41

Measurement of Activity Inhibiting HIV-1

DMSO solutions of samples of test compounds listed in Table 2 diluted to 8 different concentrations and the solution of the positive control AZT (azidothymidine, 0.15 ng/ml) are respectively added into 96 well plates, duplications are set for each of the dilutions, and negative control samples are also made. Aliquots of 100 μl 2×10⁵ cell/ml suspension are inoculated onto the 96 well cell culture plates and cultured in an incubator under a condition of 37° C., 5% CO₂ and saturated humidity. The pathologic changes of the cells are observed every day. The HIV-1 P24 antigen contents in supernatant cells are measured in 4 days (96 h) after addition of the test compounds according to the operation procedure provided by the HIV-1 P24 antigen kit. The inhibition activity of the compounds on the virus is then calculated, the results are listed in Table 2.

The invention claimed is:

1. A method of treating HIV infection, comprising administration to a subject in need thereof an effective amount of an amino-benzoyl derivative having a structure as shown in Formula (I):

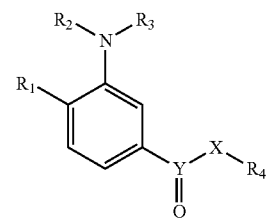

wherein R₁ is a methoxy group;
R₂ is H;
R₃ is methyl, ethyl, isopropyl, or selected from the group consisting of 2-chloroacetyl, 2-fluoroacetyl, 2-bromoacetyl, 2-chloropropionyl, 2-fluoropropionyl, 2-bromopropionyl, acetyl, propionyl, 2-bromobutyryl, methanesulfonamideacyl, trifluoroacetyl and t-butoxyformyl;
X is NH;
Y is C;
R4 is selected form the group consisting of

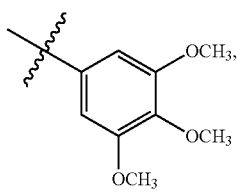 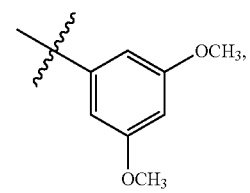

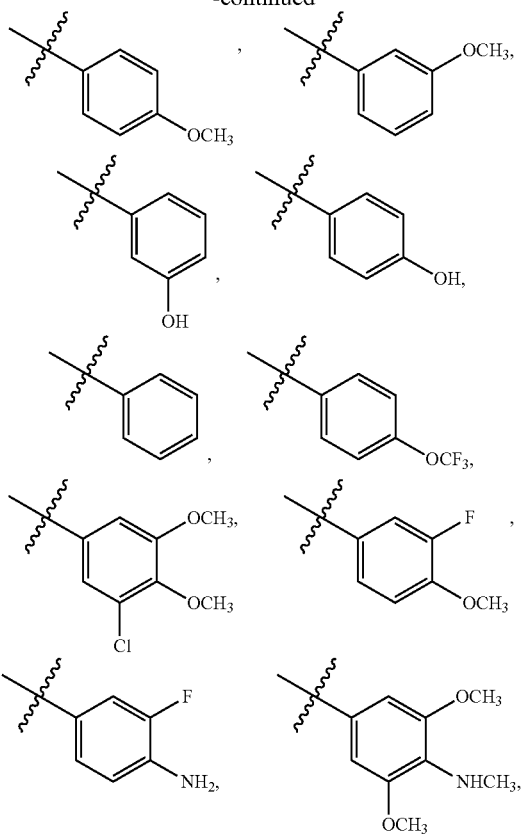
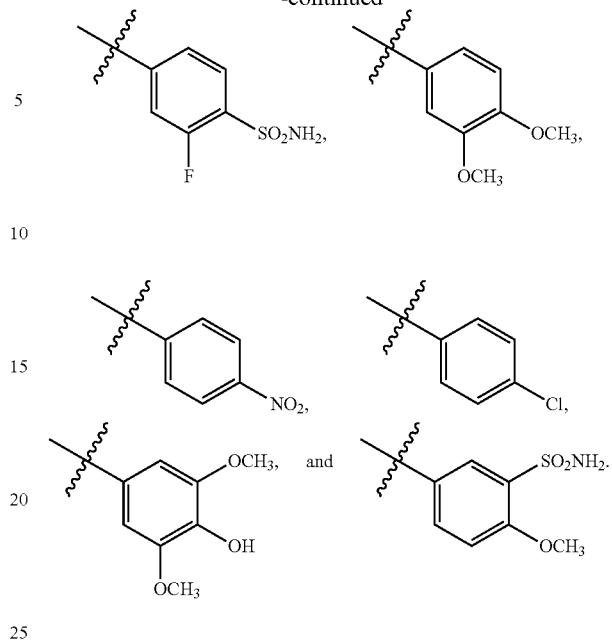
2. The method of claim 1, wherein the amino-benzoyl derivative is administered as a pharmaceutically acceptable salt.
3. The method of claim 1, wherein the amino-benzoyl derivative is administered with one or more pharmaceutically acceptable carriers.
* * * * *